(12) United States Patent
Lamoureux et al.

(10) Patent No.: US 8,187,159 B2
(45) Date of Patent: May 29, 2012

(54) THERAPEUTIC MEMBER INCLUDING A RAIL USED IN BRACHYTHERAPY AND OTHER RADIATION THERAPY

(75) Inventors: Gary A. Lamoureux, Woodbury, CT (US); James Matons, Woodbury, CT (US); Warren Johnston, Thomaston, CT (US); Matthew Bouffard, Oakville, CT (US); Warren Rice, Watertown, CT (US)

(73) Assignee: Biocompatibles, UK, Farnham, Surrey (GB)

( * ) Notice: Subject to any disclaimer, the term of this patent is extended or adjusted under 35 U.S.C. 154(b) by 764 days.

(21) Appl. No.: 12/393,349

(22) Filed: Feb. 26, 2009

(65) Prior Publication Data

US 2009/0203953 A1    Aug. 13, 2009

Related U.S. Application Data

(63) Continuation-in-part of application No. 11/489,895, filed on Jul. 20, 2006, now Pat. No. 7,972,261, which is a continuation-in-part of application No. 11/187,411, filed on Jul. 22, 2005, now Pat. No. 7,736,293.

(51) Int. Cl.
*A61M 36/00* (2006.01)
(52) U.S. Cl. .......................................... 600/8
(58) Field of Classification Search ............ 600/1–8; 252/644; 424/1.11–1.89; *A61M 36/00, 36/02, A61M 36/04, 36/12*
See application file for complete search history.

(56) References Cited

U.S. PATENT DOCUMENTS

| | | |
|---|---|---|
| 1,578,945 A | 3/1926 | Withers |
| 2,067,589 A | 1/1937 | Antrim |

(Continued)

FOREIGN PATENT DOCUMENTS

EP    0 030 822 B1    9/1983

(Continued)

OTHER PUBLICATIONS

European Patent Office, Extended European Search Report for EP 11 16 3551.2, Jul. 29, 2011, 6 pages.

(Continued)

*Primary Examiner* — Charles A Marmor, II
*Assistant Examiner* — Catherine E Burk
(74) *Attorney, Agent, or Firm* — Fliesler Meyer LLP

(57) ABSTRACT

A therapeutic member for use in brachytherapy deliverable to an implant site by way of a needle comprises a single radioactive source encapsulated by a bio-absorbable material having an outer surface including one or more ribs encircling the single radioactive source, a leading edge endcap rib and a trailing edge endcap rib. The one or more ribs reduces a tendency of the member to migrate and rotate within a patient's body after implantation. The encapsulating material further includes a first rail formed from the bio-absorbable material extending at least from opposite sides of the outer surface of the encapsulating material along the longitudinal axis of the therapeutic member, and a second rail formed from the bio-absorbable material extending at least from opposite sides of the outer surface of the encapsulating material along the longitudinal axis of the therapeutic member, the second rail arranged in a plane substantially perpendicular to a plane in which the first rail is arranged.

21 Claims, 16 Drawing Sheets

U.S. PATENT DOCUMENTS

| | | |
|---|---|---|
| 2,153,889 A | 4/1939 | Frederick |
| 2,575,138 A | 11/1951 | Slaughter |
| 2,668,162 A | 2/1954 | Lowe |
| 2,703,316 A | 3/1955 | Schneider |
| 2,758,987 A | 8/1956 | Saizberg |
| 3,187,752 A | 6/1965 | Glick |
| 3,297,033 A | 1/1967 | Schmitt et al. |
| 3,351,049 A | 11/1967 | Lawrence |
| 3,565,869 A | 2/1971 | De Prospero |
| 3,636,956 A | 1/1972 | Schneider |
| 3,752,630 A | 8/1973 | Takagi |
| 3,811,426 A | 5/1974 | Culver et al. |
| 3,839,297 A | 10/1974 | Wasserman et al. |
| 3,936,414 A | 2/1976 | Wright et al. |
| 3,993,073 A | 11/1976 | Zaffaroni |
| 4,052,988 A | 10/1977 | Doddi |
| 4,086,914 A | 5/1978 | Moore |
| 4,141,087 A | 2/1979 | Shalaby et al. |
| 4,167,179 A | 9/1979 | Kirsch |
| 4,247,406 A | 1/1981 | Widder et al. |
| 4,351,337 A | 9/1982 | Sidman |
| 4,379,138 A | 4/1983 | Pitt et al. |
| 4,402,308 A | 9/1983 | Scott |
| 4,416,308 A | 11/1983 | Bower |
| 4,416,659 A | 11/1983 | Simpson et al. |
| 4,427,005 A | 1/1984 | Tener |
| 4,441,496 A | 4/1984 | Shalaby et al. |
| 4,452,973 A | 6/1984 | Casey et al. |
| 4,473,670 A | 9/1984 | Kessidis |
| 4,509,506 A | 4/1985 | Windorski et al. |
| 4,510,295 A | 4/1985 | Bezwada et al. |
| 4,612,923 A | 9/1986 | Kronenthal |
| 4,621,638 A | 11/1986 | Silvestrini |
| 4,646,741 A | 3/1987 | Smith |
| 4,689,424 A | 8/1987 | Shalaby et al. |
| 4,697,575 A | 10/1987 | Horowitz |
| 4,700,692 A | 10/1987 | Baumgartner |
| 4,702,228 A | 10/1987 | Russell et al. |
| 4,706,652 A | 11/1987 | Horowitz |
| 4,741,337 A | 5/1988 | Smith et al. |
| 4,754,745 A | 7/1988 | Horowitz |
| 4,763,642 A | 8/1988 | Horowitz |
| 4,763,671 A | 8/1988 | Goffinet |
| 4,772,287 A | 9/1988 | Ray et al. |
| 4,784,116 A | 11/1988 | Russell et al. |
| 4,815,449 A | 3/1989 | Horowitz |
| 4,820,844 A | 4/1989 | Kagiya et al. |
| 4,847,505 A | 7/1989 | Suthanthiran |
| 4,891,165 A | 1/1990 | Suthanthiran |
| 4,916,209 A | 4/1990 | Fung et al. |
| 4,936,823 A | 6/1990 | Colvin et al. |
| 4,946,435 A | 8/1990 | Suthanthiran et al. |
| 5,022,940 A | 6/1991 | Mehoudar |
| 5,030,195 A | 7/1991 | Nardi |
| 5,059,166 A | 10/1991 | Fischell et al. |
| 5,242,373 A | 9/1993 | Scott et al. |
| 5,264,540 A | 11/1993 | Cooper et al. |
| 5,296,229 A | 3/1994 | Grandjean |
| 5,339,812 A | 8/1994 | Hardy et al. |
| 5,342,283 A | 8/1994 | Good |
| 5,391,139 A | 2/1995 | Edmundson |
| 5,397,816 A | 3/1995 | Reilly et al. |
| 5,403,576 A | 4/1995 | Lin et al. |
| 5,405,309 A | 4/1995 | Carden |
| 5,424,288 A | 6/1995 | Order |
| 5,460,592 A | 10/1995 | Langton et al. |
| 5,486,360 A | 1/1996 | Ballagh et al. |
| 5,521,280 A | 5/1996 | Reilly et al. |
| 5,538,726 A | 7/1996 | Order |
| 5,595,979 A | 1/1997 | Snyder |
| 5,620,700 A | 4/1997 | Berggren et al. |
| 5,626,829 A | 5/1997 | Koutrouvelis |
| 5,626,862 A | 5/1997 | Brem et al. |
| 5,650,442 A | 7/1997 | Mitchell et al. |
| 5,713,828 A | 2/1998 | Coniglione |
| 5,755,704 A | 5/1998 | Lunn |
| 5,761,877 A | 6/1998 | Quandt |
| 5,762,950 A | 6/1998 | Yli-Urpo et al. |
| 5,833,593 A | 11/1998 | Liprie |
| 5,860,909 A | 1/1999 | Mick et al. |
| 5,871,437 A | 2/1999 | Alt |
| 5,886,026 A | 3/1999 | Hunter et al. |
| 5,916,998 A | 6/1999 | Ferruti et al. |
| 5,928,130 A | 7/1999 | Schmidt |
| 5,938,583 A | 8/1999 | Grimm |
| 6,007,475 A | 12/1999 | Slater et al. |
| 6,010,446 A | 1/2000 | Grimm |
| 6,011,092 A | 1/2000 | Seppala et al. |
| 6,030,333 A | 2/2000 | Sioshansi et al. |
| 6,039,684 A | 3/2000 | Ildstad et al. |
| 6,040,408 A | 3/2000 | Koole |
| 6,053,858 A | 4/2000 | Bueche et al. |
| 6,080,099 A | 6/2000 | Slater et al. |
| 6,086,942 A | 7/2000 | Carden et al. |
| 6,099,457 A | 8/2000 | Good |
| 6,099,458 A | 8/2000 | Robertson |
| 6,102,844 A | 8/2000 | Ravins |
| 6,132,359 A | 10/2000 | Bolenbaugh |
| 6,132,677 A | 10/2000 | Ohriner |
| 6,132,947 A | 10/2000 | Honan et al. |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater et al. |
| 6,213,932 B1 | 4/2001 | Schmidt |
| 6,228,969 B1 | 5/2001 | Lee et al. |
| 6,241,962 B1 | 6/2001 | Nicolini et al. |
| 6,248,057 B1 | 6/2001 | Mavity et al. |
| 6,251,135 B1 | 6/2001 | Stinson et al. |
| 6,264,599 B1 | 7/2001 | Slater et al. |
| 6,264,600 B1 | 7/2001 | Grimm |
| 6,273,851 B1 | 8/2001 | Slater et al. |
| 6,283,911 B1 | 9/2001 | Keren |
| 6,290,982 B1 | 9/2001 | Seppala et al. |
| 6,312,374 B1 | 11/2001 | von Hoffmann |
| 6,319,190 B1 | 11/2001 | Schmidt et al. |
| 6,327,490 B1 | 12/2001 | Spetz |
| 6,358,195 B1 | 3/2002 | Green et al. |
| 6,360,116 B1 | 3/2002 | Jackson et al. |
| 6,387,034 B1 | 5/2002 | Lee |
| 6,391,279 B1 | 5/2002 | Singh et al. |
| 6,398,709 B1 | 6/2002 | Ehr et al. |
| 6,403,916 B1 | 6/2002 | Spooner et al. |
| 6,419,621 B1 | 7/2002 | Sioshansi et al. |
| 6,426,145 B1 | 7/2002 | Moroni |
| 6,428,504 B1 | 8/2002 | Riaziat et al. |
| 6,436,026 B1 | 8/2002 | Sioshansi et al. |
| 6,438,401 B1 | 8/2002 | Cheng et al. |
| 6,440,058 B1 | 8/2002 | Cutrer |
| 6,450,937 B1 | 9/2002 | Mercereau et al. |
| 6,450,938 B1 | 9/2002 | Miller |
| 6,450,939 B1 | 9/2002 | Grimm |
| 6,471,631 B1 | 10/2002 | Slater et al. |
| 6,472,675 B2 | 10/2002 | White et al. |
| 6,474,535 B1 | 11/2002 | Shanks et al. |
| 6,482,178 B1 | 11/2002 | Andrews et al. |
| 6,497,646 B1 | 12/2002 | Candelaria et al. |
| 6,500,109 B2 | 12/2002 | Tokita et al. |
| 6,514,193 B2 | 2/2003 | Kaplan |
| 6,537,193 B1 | 3/2003 | Lennox |
| 6,539,247 B2 | 3/2003 | Spetz |
| 6,549,802 B2 | 4/2003 | Thornton |
| 6,554,760 B2 | 4/2003 | Lamoureux et al. |
| 6,561,967 B2 | 5/2003 | Schmidt |
| 6,572,525 B2 | 6/2003 | Yoshizumi |
| 6,572,527 B2 | 6/2003 | Steele et al. |
| 6,575,888 B2 | 6/2003 | Zamora et al. |
| 6,585,633 B2 | 7/2003 | Vitali et al. |
| 6,595,908 B2 | 7/2003 | Loffler et al. |
| 6,599,231 B1 | 7/2003 | Hoedeman et al. |
| 6,612,976 B2 | 9/2003 | Rosenthal et al. |
| 6,616,593 B1 | 9/2003 | Elliott et al. |

| | | |
|---|---|---|
| 6,616,594 B2 | 9/2003 | Fontayne et al. |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,621 B2 | 12/2003 | O'Hara et al. |
| 6,669,622 B2 | 12/2003 | Reed et al. |
| 6,679,824 B1 | 1/2004 | Reed et al. |
| 6,682,471 B2 | 1/2004 | Steele et al. |
| 6,689,043 B1 | 2/2004 | McIntire et al. |
| 6,709,381 B2 | 3/2004 | Munro |
| 6,716,156 B2 | 4/2004 | Menuhr et al. |
| 6,719,242 B2 | 4/2004 | Floyd et al. |
| 6,723,037 B2 | 4/2004 | Hamazaki et al. |
| 6,723,052 B2 | 4/2004 | Mills |
| 6,726,617 B1 | 4/2004 | Schmidt |
| 6,746,661 B2 | 6/2004 | Kaplan |
| 6,749,554 B1 | 6/2004 | Snow et al. |
| 6,752,753 B1 | 6/2004 | Hoskins et al. |
| 6,755,775 B2 | 6/2004 | Kalas et al. |
| 6,761,680 B2 | 7/2004 | Terwilliger et al. |
| 6,786,858 B2 | 9/2004 | Terwilliger et al. |
| 6,790,170 B2 | 9/2004 | Moody et al. |
| 6,800,055 B2 | 10/2004 | Amols et al. |
| 6,805,898 B1 | 10/2004 | Wu et al. |
| 6,820,318 B2 | 11/2004 | Terwilliger et al. |
| 6,837,844 B1 | 1/2005 | Ellard et al. |
| 6,846,283 B2 | 1/2005 | Green et al. |
| 6,905,455 B2 | 6/2005 | Rapach et al. |
| 6,911,000 B2 | 6/2005 | Mick et al. |
| 6,926,657 B1 | 8/2005 | Reed et al. |
| 6,949,064 B2 | 9/2005 | Lowery et al. |
| 6,969,344 B2 | 11/2005 | Drobnik et al. |
| 6,989,543 B2 | 1/2006 | Drobnik et al. |
| 7,008,367 B2 | 3/2006 | Visscher et al. |
| 7,074,291 B2 | 7/2006 | Terwilliger et al. |
| 7,083,566 B2 | 8/2006 | Tornes et al. |
| 7,094,198 B2 | 8/2006 | Terwilliger et al. |
| 7,118,523 B2 | 10/2006 | Loffler et al. |
| 7,211,039 B2 | 5/2007 | Lamoureux et al. |
| 7,267,643 B2 | 9/2007 | Koster et al. |
| 7,322,928 B2 | 1/2008 | Reed et al. |
| 7,497,818 B2 | 3/2009 | Terwilliger et al. |
| 7,601,113 B2 | 10/2009 | Lebovic et al. |
| 7,776,310 B2 * | 8/2010 | Kaplan .................. 424/1.25 |
| 2001/0044567 A1 | 11/2001 | Zamora et al. |
| 2001/0047185 A1 | 11/2001 | Satz |
| 2002/0055666 A1 | 5/2002 | Hunter et al. |
| 2002/0055667 A1 | 5/2002 | Mavity et al. |
| 2002/0058854 A1 | 5/2002 | Reed et al. |
| 2002/0066824 A1 | 6/2002 | Floyd et al. |
| 2002/0114763 A1 | 8/2002 | Glajch et al. |
| 2002/0123660 A1 | 9/2002 | Amols et al. |
| 2002/0156338 A1 | 10/2002 | Menuhr et al. |
| 2003/0003094 A1 | 1/2003 | Hunter et al. |
| 2003/0084988 A1 | 5/2003 | Terwilliger et al. |
| 2003/0092958 A1 | 5/2003 | Terwilliger et al. |
| 2003/0132546 A1 | 7/2003 | Yamaguchi et al. |
| 2003/0139567 A1 | 7/2003 | Kim et al. |
| 2003/0144570 A1 | 7/2003 | Hunter et al. |
| 2003/0153804 A1 | 8/2003 | Tornes et al. |
| 2003/0181794 A1 | 9/2003 | Rini et al. |
| 2003/0191355 A1 | 10/2003 | Ferguson |
| 2004/0024453 A1 | 2/2004 | Castillejos |
| 2004/0109823 A1 | 6/2004 | Kaplan |
| 2004/0158117 A1 | 8/2004 | Drobnik et al. |
| 2004/0158118 A1 * | 8/2004 | Drobnik et al. .................. 600/8 |
| 2004/0225174 A1 | 11/2004 | Fuller et al. |
| 2005/0049490 A1 | 3/2005 | Mills |
| 2005/0261541 A1 | 11/2005 | Henderson et al. |
| 2006/0015068 A1 | 1/2006 | Amisar et al. |
| 2006/0052654 A1 | 3/2006 | Drobnik et al. |
| 2006/0063960 A1 | 3/2006 | Wissman et al. |
| 2006/0094983 A1 | 5/2006 | Burbank et al. |
| 2006/0121080 A1 | 6/2006 | Lye et al. |
| 2006/0177379 A1 | 8/2006 | Asgari |
| 2006/0224035 A1 | 10/2006 | Russell, Jr. et al. |
| 2007/0224234 A1 | 9/2007 | Steckel et al. |
| 2007/0238983 A1 | 10/2007 | Suthanthiran et al. |
| 2007/0270781 A1 | 11/2007 | Burgermeister et al. |
| 2008/0208127 A1 | 8/2008 | Kuriyama et al. |

FOREIGN PATENT DOCUMENTS

| | | |
|---|---|---|
| EP | 0 292 630 A | 11/1988 |
| EP | 0 466 681 B1 | 1/1992 |
| EP | 0 668 088 A | 8/1995 |
| EP | 0 993 843 A | 4/2000 |
| EP | 1 240 920 A | 9/2002 |
| WO | WO 95/03036 | 2/1995 |
| WO | WO 96/05872 | 2/1996 |
| WO | WO 96/14880 | 5/1996 |
| WO | WO 97/19706 | 6/1997 |
| WO | WO 00/64538 | 2/2000 |
| WO | WO 00/32238 | 6/2000 |
| WO | WO 00/41185 | 7/2000 |
| WO | WO 00/43045 | 7/2000 |
| WO | WO 00/51639 | 9/2000 |
| WO | WO 00/57923 | 10/2000 |
| WO | WO 00/61229 | 10/2000 |
| WO | WO 01/36007 | 5/2001 |
| WO | WO 02/30472 | 4/2002 |
| WO | WO 03/066705 | 8/2003 |
| WO | WO 2004/026111 A2 | 4/2004 |
| WO | WO 2008/106586 | 9/2008 |
| WO | WO 2009/097408 A1 | 8/2009 |

OTHER PUBLICATIONS

Cron, et al., "Changes in the tumor microenvironment during low-dose-rate permanent seed implantation iodine-125 brachytherapy," Int. J. Radiat. Oncol. Biol. Phys., 63(4): 1245-51 (2005).

Gacci, et al., "PSA recurrence after brachytherapy for seed misplacement: a double-blind radiologic and pathologic work-up after salvage prostatectomy," Prostate Cancer Prostatic Dis. 11(1): 99-101 (2008). (epub., Oct. 1-3, 2007).

Helpap, "Fundamentals on the pathology of prostatic carcinoma after brachytherapy," World J. Urol., 20(4): 207-12 (2002).

Information Disclosure Statements filed in U.S. Appl. No. 10/665,793, 13 pages.

Merrick, et al., "Seed Fixity in the Prostate/Periprostatic Region Following Brachytherapy," IJROBP vol. 46(1): 215-220 (2000).

Poggi, et al., "Marker Seed Migration in Prostate Localization," IJROBP vol. 56(5): 1248-1251 (2003).

Tapen, et al., "Reduction of Radioactive Seed Embolization to the Lung Following Prostate Brachytherapy," IJROBP vol. 42(5): 1063-1067 (1998).

Miller, R., "Advances May Improves Prostate Cancer Treatment," Board of Regents of the University of Wisconsin System, http://www.news.wisc.edu/11899.html, 3 pages (Dec. 1, 2005).

Martinez, A.., et al., "Sterilization of 125I Seeds Encased in Vicryl Sutures for Permanent Interstitial Implantation"; IJROBP vol. 5: 411-413 (1979).

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm. "Mentor Acquires Breakthrough Brachytherapy Technology" (Jan.25, 2002).

Medi-Physics brochure entitled I-125 Seeds. No. 6711, Medi-Physics, Inc. Arlington Heights Il. 60004, USA; Revised. Oct. 1999, 2 pages.

Medi-Physics brochure entitled I-125 Seeds. No. 7000; Medi-Physics, Inc. Arlington Heights Il. 60004, USA; Revised. Oct. 1999, 2 pages.

Amersham Health; "EchoSeed™"; http://www.amersharnhealth-us.com/echoseed/ printed no. 19, 2003.

Amersham Health; "Rapid Strand Indications" Http;//www.amershamhealth-us.com/products/index.htp?a=i&i=38;printed Nov. 19, 2003.

Amersham Health; OncoSeed™ (Iodine-125 Seeds) http://www.amershamhealty-us.com/oncoseed/; printed Nov. 19, 2003

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

International Search Report for PCT/US2010/025113 dated Feb. 23, 2010; 8 pages.

\* cited by examiner

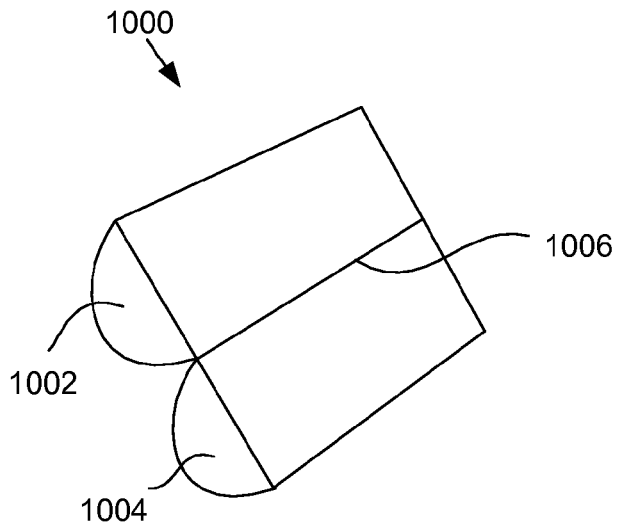
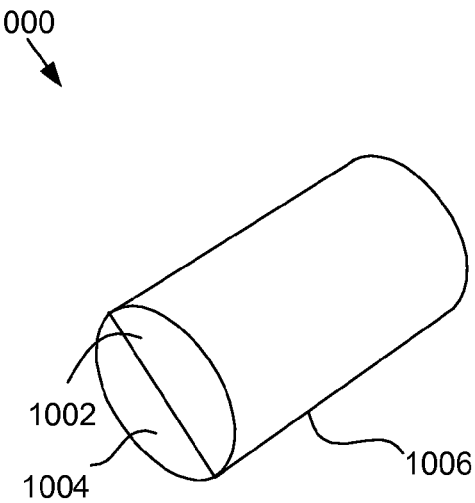
FIG. 10A
FIG. 10B
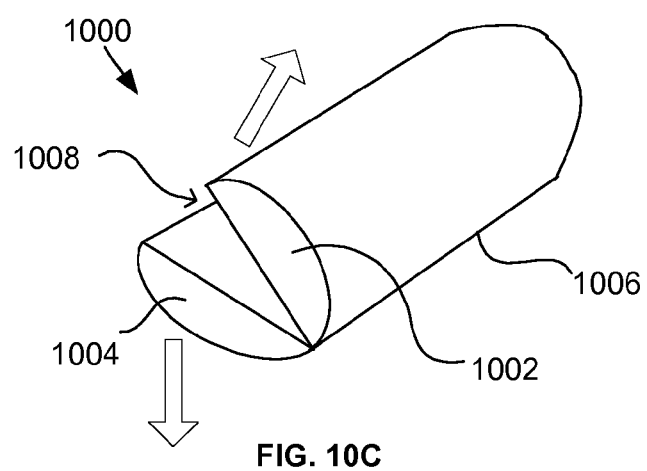
FIG. 10C

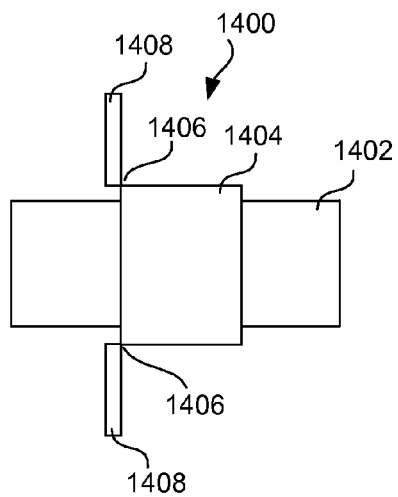
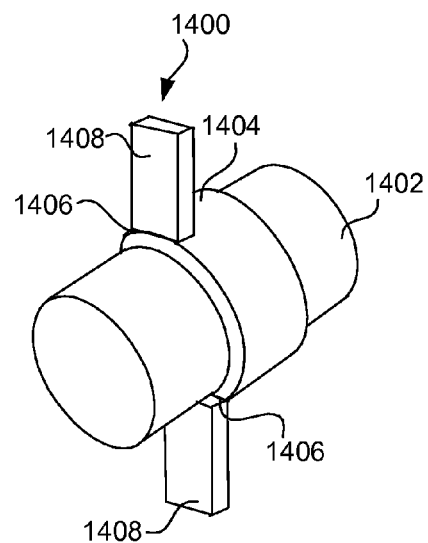
FIG. 14A                FIG. 14B
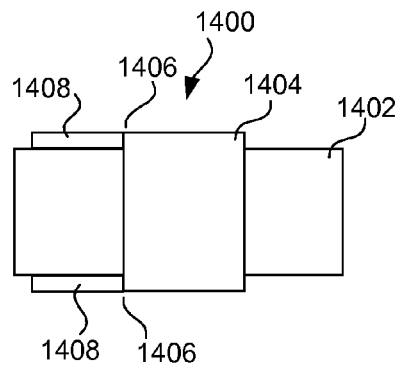
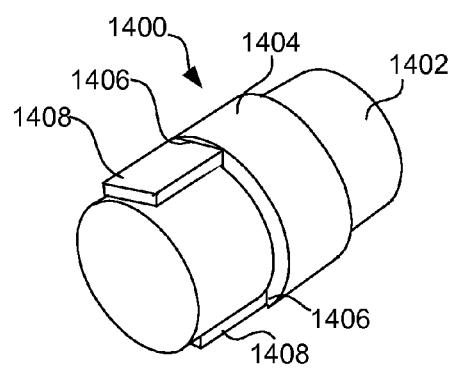
FIG. 14C                FIG. 14D

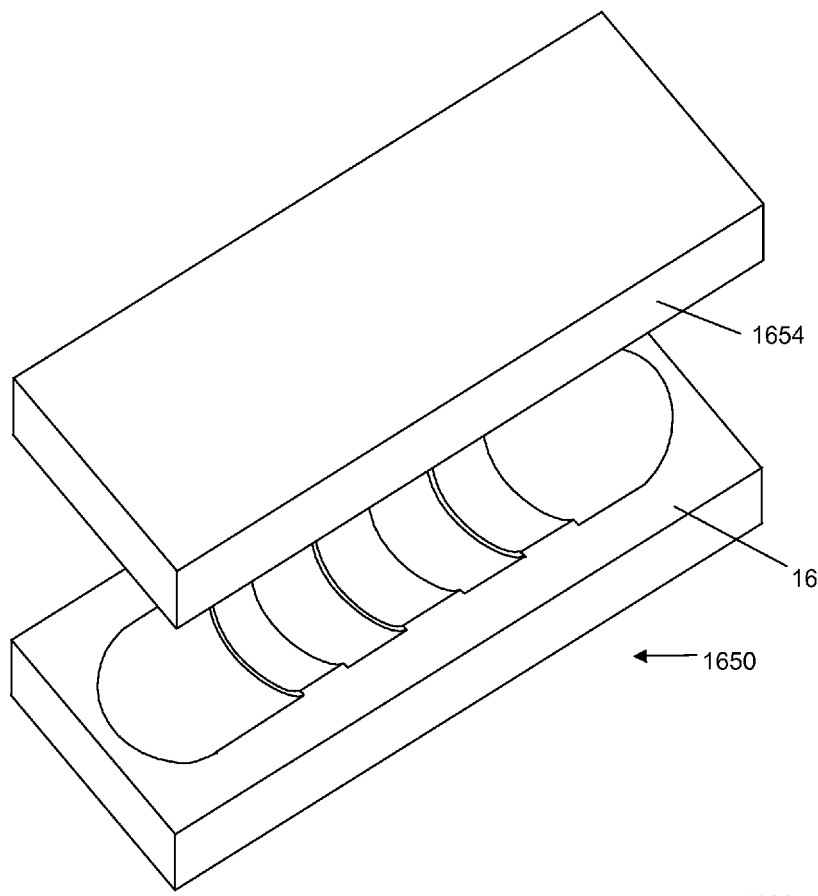
FIG. 16A
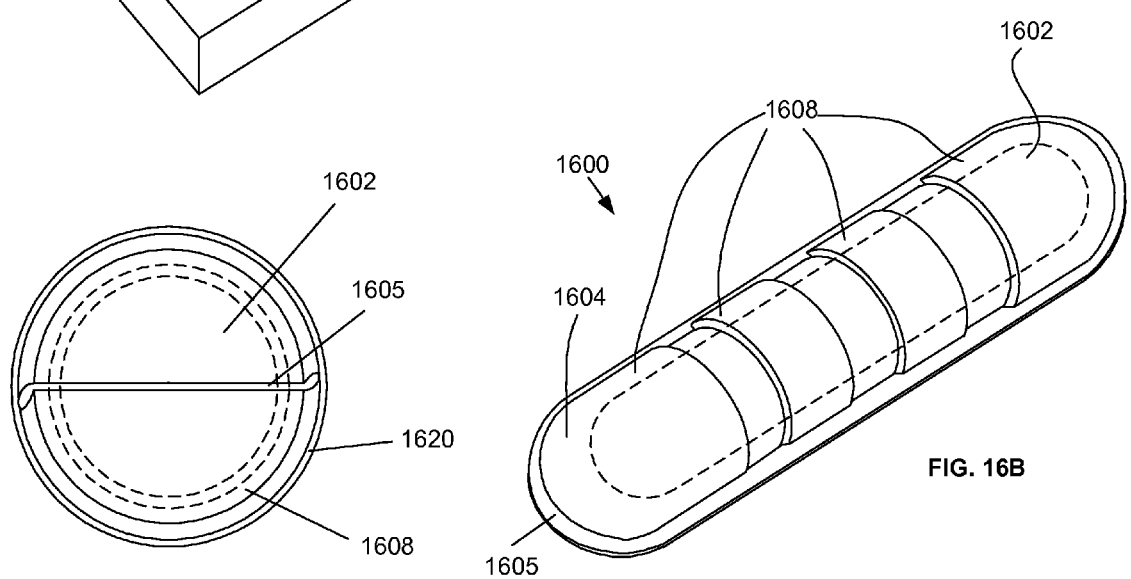
FIG. 16B
FIG. 16C

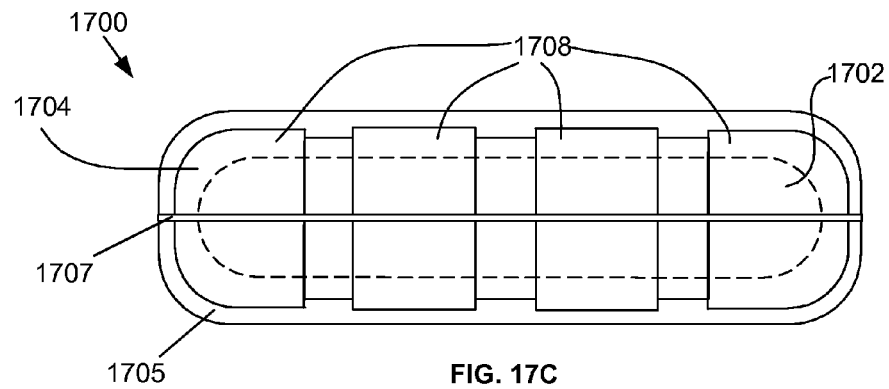
FIG. 17C
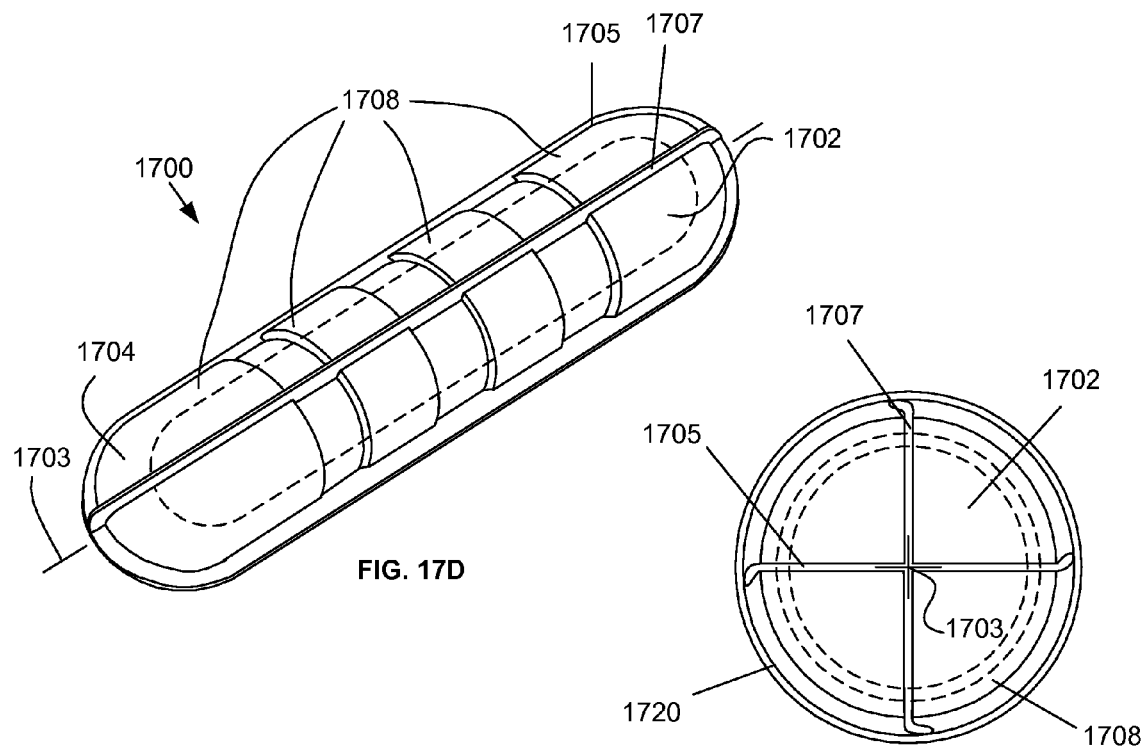
FIG. 17D
FIG. 17E ized or otherwise treated surface. For example, the '176 patent teaches sandblasting the exterior of the seed container. However, sandblasting can strip material away from the exterior of the container, weakening it, and potentially forming small holes through which the radioisotope may be exposed to the body. Further, although the '176 patent teaches that the textured surface may assist in lodging the seed in place at its desired position within the tissue, the '176 patent does not address the problem of rotation of the seed within the tissue, which is undesirable for the reasons discussed previously.

THERAPEUTIC MEMBER INCLUDING A RAIL USED IN BRACHYTHERAPY AND OTHER RADIATION THERAPY

PRIORITY CLAIM

This application is a continuation-in-part (CIP) of U.S. patent application Ser. No. 11/489,895, filed Jul. 20, 2006, and entitled DEVICES TO RESIST MIGRATION AND ROTATION OF IMPLANTS USED IN BRACHYTHERAPY AND OTHER RADIATION THERAPY, which issued as U.S. Pat. No. 7,972,261, which is a continuation-in-part (CIP) of U.S. patent application Ser. No. 11/187,411, filed Jul. 22, 2005, and entitled IMPLANTS FOR USE IN BRACHYTHERAPY AND OTHER RADIATION THERAPY THAT RESIST MIGRATION AND ROTATION, which issued as U.S. Pat. No. 7,736,293, all of which are incorporated herein by reference.

FIELD OF THE INVENTION

This invention relates to radiotherapy. More particularly, it relates to implants for use in brachytherapy, and in particular to therapeutic members, spacers and strands that are used to resist migration and rotation of radioactive sources, and features to resist movement of such implants within needles used for delivering the implants to treatment sites.

BACKGROUND

Brachytherapy is a general term covering medical treatment which involves placement of radioactive sources near a diseased tissue and may involve the temporary or permanent implantation or insertion of radioactive sources into the body of a patient. The radioactive sources are thereby located in proximity to the area of the body which is being treated. This has the advantage that a high dose of radiation may be delivered to the treatment site with relatively low doses of radiation to surrounding or intervening healthy tissue. Exemplary radioactive sources include radioactive seeds, radioactive rods and radioactive coils.

Brachytherapy has been used or proposed for use in the treatment of a variety of conditions, including arthritis and cancer. Exemplary cancers that may be treated using brachytherapy include breast, brain, liver and ovarian cancer and especially prostate cancer in men. For a specific example, treatment for prostate cancer may involve the temporary implantation of radioactive sources (e.g., rods) for a calculated period, followed by their subsequent removal. Alternatively, the radioactive sources (e.g., seeds) may be permanently implanted in the patient and left to decay to an inert state over a predictable time. The use of temporary or permanent implantation depends on the isotope selected and the duration and intensity of treatment required.

Permanent implants for prostate treatment include radioisotopes with relatively short half lives and lower energies relative to temporary seeds. Exemplary permanently implantable sources include iodine-125, palladium-103 or cesium-131 as the radioisotope. The radioisotope can be encapsulated in a biocompatible casing (e.g., a titanium casing) to form a "seed" which is then implanted. Temporary implants for the treatment of prostate cancer may involve iridium-192 as the radioisotope. For temporary implants, radioactive rods are often used.

Conventional radioactive seeds are typically smooth sealed containers or capsules of a biocompatible material, e.g., titanium or stainless steel, containing a radioisotope within the sealed chamber that permits radiation to exit through the container/chamber walls. Other types of implantable radioactive sources for use in radiotherapy are radioactive rods and radioactive coils, as mentioned above.

Preferably, the implantation of radioactive sources for brachytherapy is carried out using minimally-invasive techniques such as, e.g., techniques involving needles and/or catheters. It is possible to calculate a desired location for each radioactive source which will give the desired radiation dose profile. This can be done using knowledge of the radioisotope content of each source, the dimensions of the source, accurate knowledge of the dimensions of the tissue or tissues in relation to which the source is to be placed, plus knowledge of the position of the tissue relative to a reference point. The dimensions of tissues and organs within the body for use in such dosage calculations may be obtained prior to or during placement of the radioactive sources by using conventional diagnostic imaging techniques including X-ray imaging, magnetic resonance imaging (MRI), computed tomography (CT) imaging, fluoroscopy and ultrasound imaging.

During the placement of the radioactive sources into position, a surgeon can monitor the position of tissues such as the prostate gland using, e.g., ultrasound imaging or fluoroscopy techniques which offer the advantage of low risk and convenience to both patient and surgeon. The surgeon can also monitor the position of the relatively large needle used in implantation procedures using ultrasound or other imaging.

Once implanted, radioactive sources (e.g., seeds, rods or coils) are intended to remain at the site of implantation. However, the radioactive sources may on some occasions migrate within a patient's body away from the initial site of implantation. This is undesirable from a clinical perspective, as migration may lead to underdosing of a tumor or other diseased tissue and/or exposure of healthy tissue to radiation. Additionally, there have been reported incidents where a migrated seed implant has caused a pulmonary embolism. Accordingly, there is a need to reduce the tendency for radioactive sources to migrate within a patient's body.

Radioactive sources may also on some occasions rotate or twist from the original orientation at which the seed was implanted. This is also undesirable from a clinical perspective, because the radiation pattern of the sources may be directional, thereby causing underdosing or overdosing of a tumor or other diseased tissue and/or exposure of healthy tissue to radiation. Accordingly, there is also a need to reduce the tendency for radioactive sources to rotate within a patient's body.

Efforts have been made to reduce the tendency for radioactive seeds to migrate within a patient's body. For example, U.S. Pat. No. 6,632,176 discloses a radioactive seed having a biocompatible container with at least one part of a surface of the container being roughened, shaped or otherwise treated so that it is no longer smooth. According to the '176 patent, the roughening, shaping or other treatment is achieved by: forcing the seed container through a ridged or serrated dye or a threading device to impart grooves on the outer surface of the container; milling the seed container; using a wire brush, file, or sandpaper to roughen the outer surface of the container; etching using a laser or water-jet cutter, or by electrolytic etching; blasting (e.g., sand blasting); or electroplating.

Disadvantages of the radioactive seeds disclosed in the '176 patent is that they are not off the shelf seeds, but rather, are custom seeds whose manufacturing cost is likely higher than that of a typical radioactive seed. Additionally, even though the '176 patent says that the treatment process should not compromise the integrity of the container, the integrity of the container may indeed be affected by the roughing, shaping and other treatments suggested in the '176 patent. Additionally, because the containers themselves are being changed, the radioactive seeds having such roughened, shaped or otherwise treated containers may be subject to government certification or re-certification. Further, the modified containers may affect the directional radiation pattern of the seed, potentially resulting in adverse clinical results. Accordingly, it is preferred that the means of reducing the tendency for radioactive seeds to migrate and/or rotate within a patient's body overcome the above mentioned disadvantages.

When performing external beam radiation procedures such as intensity modulated radiation therapy (IMRT) and conformal radiation therapy (CRT) it is important that a target for radiation be accurately identified. To accomplish this, radiopaque markers (sometime referred to as fiducial or fiduciary markers) are often implanted into the patient at or near the target, so that the radiation can be accurately focused. Once implanted, such markers are intended to remain at the site of implantation. However, the markers may on some occasions migrate and/or rotate within a patient's body away from the initial site of implantation. This is undesirable because it is the locations of the markers that are used to determine where to focus the radiation treatments. Accordingly, there is a need to reduce the tendency for such markers to migrate and/or rotate within a patient's body.

SUMMARY OF THE INVENTION

Embodiments of the present invention are directed to therapeutic members and strands for use in brachytherapy. Such members and strands, as will be understood from the detailed description, are designed to reduce the tendency for the members and strands (and thus the radioactive sources therein) to migrate and/or rotate within a patient's body.

In one embodiment a member includes a radioactive source and a material that encapsulates the radioactive source. Such encapsulating material, which is preferably, but not necessarily, bioabsorbable, is likely polymeric or some other plastic material. An outer surface of the encapsulating material includes at least one protrusion, and preferably a plurality of protrusions, to reduce the tendency of the member to migrate and rotate within a patient's body after implantation.

In accordance with an embodiment, one or more of the protrusions extend in a radial direction (e.g., perpendicular or at an acute angle) with respect to a longitudinal axis of the radioactive source. One or more protrusions may also extend in a longitudinal direction with respect to the radioactive source. Such protrusions can have various shapes, such as, but not limited to, square, rectangular, circular, oval, triangular, pyramidal and semi-spherical, or combinations thereof.

In accordance with an embodiment, the one or more protrusions include one or more ribs that form one or more rings or a helix about a radial circumference of the radioactive source.

In accordance with another embodiment, the plurality of protrusions forms an irregular pattern on the outer surface of the encapsulating polymeric material. For example, the plurality of protrusions can form a surface that resembles a rough stucco surface.

In another embodiment, the encapsulating material is used to form an anchor mechanism that extends from at least one of the longitudinal ends of the radioactive seed to reduce a tendency of the member to migrate and rotate within a patient's body after implantation. In accordance with an embodiment, a void is formed between the anchor mechanism and the portion of the material that encapsulates the radioactive source, to allow patient tissue to enter the void after implantation.

Embodiments of the present invention are also directed to spacers, which are used to separate radioactive sources from one another, wherein the spacers include protrusions and/or anchor mechanisms, similar to those described above.

Embodiments of the present invention are also directed to strands that include protrusions and/or anchor mechanisms, similar to those described above. Such strands include a plurality of radioactive sources that are spaced apart from one another at desired intervals.

Embodiments of the present invention are also directed to spacers and strands that include portions that are biased to open after implantation, to thereby engage surrounding tissue.

Embodiments of the present invention are also directed to radiopaque markers that include protrusions and/or anchor mechanisms, similar to those described above, to reduce the tendency of the markers to migrate and rotate within a patient's body after implantation.

Embodiments of the present invention are also directed to an anchor mechanism that includes a sleeve to fit around a structure, such as a radioactive source, a thermal ablation implant, a spacer, a strand or a radiopaque marker. One or more wing is connected to the sleeve by a corresponding living hinge that enables the wing to be folded against the structure during implantation of the structure in a patient. The living hinge biases the wing such that one end of the wing moves away from the structure to engage surrounding patient tissue after implantation of the structure into a patient. This engagement of the wing with the tissue reduces a tendency for the structure to migrate and rotate after implantation.

Embodiments of the present invention are also directed to an anchor mechanism that includes a sleeve to fit around a structure, such as a radioactive source, a thermal ablation implant, a spacer, a strand or a radiopaque marker. The sleeve has a bore that extends an entire longitudinal length of the sleeve, and through which the structure fits, such that a portion of the structure can extend out from each longitudinal end of the sleeve. One or more protrusion extends from an outer surface of the sleeve to engage surrounding patient tissue after implantation of the structure into a patient, to thereby reduce a tendency for the structure to migrate and rotate after implantation.

Embodiments of the present invention are also directed to a therapeutic member for use in brachytherapy deliverable to an implant site by way of a needle that includes a radioactive source at least partially encapsulated by an outer structure formed from a bio-absorbable material. A rail extends from the outer structure, the rail formed from the bio-absorbable material. In certain embodiments, the rail is at least partially collapsed when the therapeutic member is positioned within the needle, and is elastically urged against an inner diameter of the needle to resist movement of the therapeutic member within the needle.

This summary is not intended to be a complete description of the invention. Other features, aspects, objects and advantages of the invention can be obtained from a review of the specification, the figures, and the claims.

BRIEF DESCRIPTION OF THE DRAWINGS

FIG. 10A is a perspective view of a spacer according to an embodiment of the present invention, in an open position; FIG. 10B is a perspective view of the spacer in FIG. 10A in a closed position; and FIG. 10C is a perspective view of the spacer of FIGS. 10A and 10B in a partially opened position.

FIG. 14A is a side view illustrating an anchor mechanism according to an embodiment of the present invention, it its closed position; FIG. 14B is a perspective view of the anchor mechanism of FIG. 14A, in its closed position; FIG. 14C is a side view of the anchor mechanism of FIGS. 14A and 14B, in its open position; and FIG. 14D is a perspective view of the anchor mechanism of FIGS. 14A-C, in its open position.

FIG. 16A is a perspective view of a mold for forming a therapeutic member according to an embodiment of the present invention.

FIG. 16B is a perspective view of the therapeutic member formed in the exemplary mold of FIG. 16A including a rail at least partially formed by flash from a molding process.

FIG. 16C is a front view of the therapeutic member of FIG. 16B positioned within a needle for delivery to a target site.

FIG. 17C is a side view of a therapeutic member according to a further embodiment of the present invention; and FIG. 17D is a perspective view of the therapeutic member shown in FIG. 17C.

FIG. 17E is a front view of the therapeutic member of FIGS. 17C and 17D positioned within a needle for delivery to a target site.

DETAILED DESCRIPTION

Figure 1A:
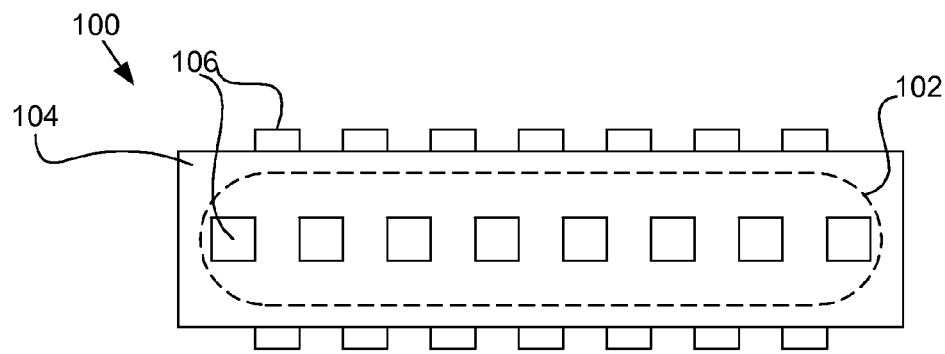
FIG. 1A is a side view of a therapeutic member according to an embodiment of the present invention.
Figure 1B:
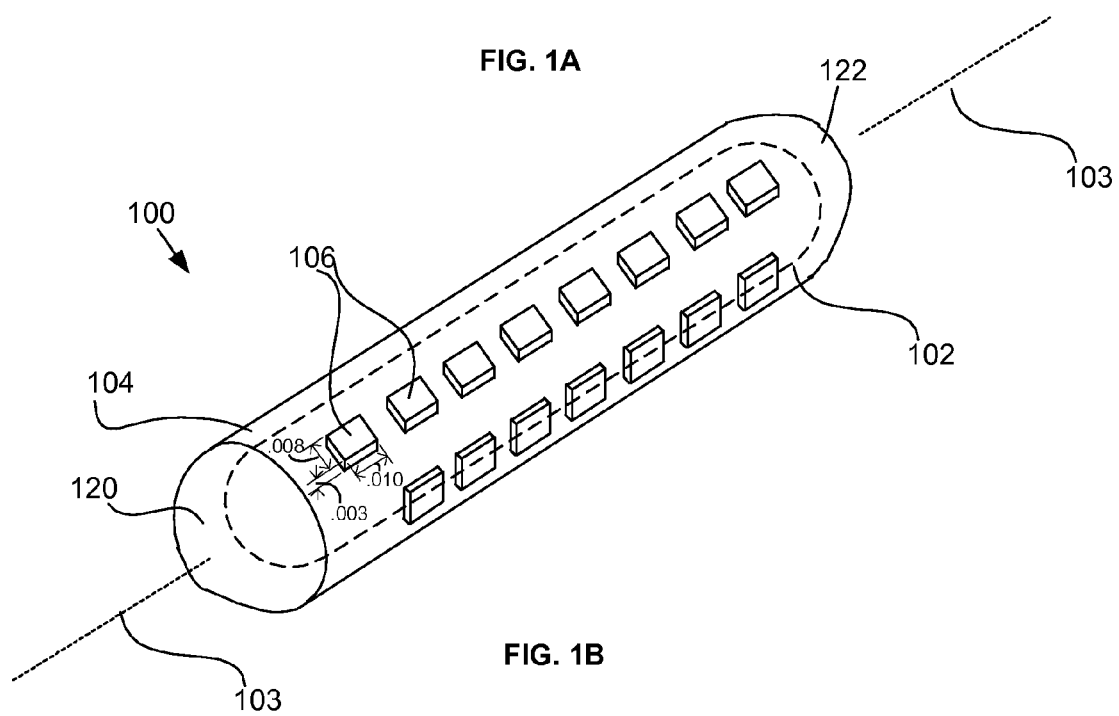
FIG. 1B is a perspective view of the therapeutic member shown in FIG. 1A.

Embodiments of the present invention relate to therapeutic members for use in treatments such as brachytherapy. As shown in FIGS. 1A and 1B, each member 100 includes a radioactive source 102 (shown in dashed line) and a material 104 that encapsulates the radioactive source 102. The radioactive source 102 can be a radioactive seed, a radioactive rod, or a radioactive coil, but is not limited thereto. The material 104 is preferably, but not necessarily, bioabsorbable. In accordance with an embodiment, the material 104 is also bioadherent. Additionally, the material 104 is preferably a polymeric material or some other plastic. Also shown in FIG. 1 is that an outer surface of the encapsulating material 104 includes protrusions 106 to reduce a tendency of the member 100 to migrate and rotate within a patient's body after implantation. Also shown in FIG. 1B (in dotted line) is a longitudinal axis of the radioactive source 102, which is also the longitudinal axis of the therapeutic member 100. The overall shape of the therapeutic member 100, excluding the protrusions 106, can be cylindrical with flat ends 120 and 122, cylindrical with rounded (e.g., bullet shaped) ends 120 and 122 or rectangular, but is not limited thereto.

The protrusions that are used to reduce a tendency of the member to migrate and rotate can be of any number of different shapes and sizes, or combinations thereof. For example, in FIGS. 1A and 1B the protrusions 106 are shown as being square or rectangular knobs that cause the outer surface of the therapeutic member 100 to resemble a knobby tire. The protrusions 106 can form a plurality of rows (e.g., four rows) which are regularly spaced about the member 100, e.g., with each row extending in a direction that is 90 degrees from the adjacent rows. Alternatively, the protrusions can protrude in a more random or irregular fashion.

Exemplary dimensions for one of the protrusions 106 in FIG. 1B is shown as being 0.010×0.008×0.003 inches. All of the protrusions 106 can have similar dimensions, or the dimensions of the protrusions may vary. For example, it is possible that the protrusions within a row have similar dimensions, but the dimensions differ for different rows. For a more specific example, another row of protrusions 106 have dimensions of 0.006×0.005×0.002 inches. These are just a few examples. One of ordinary skill in the art will appreciate from this description that the protrusions can have other dimensions while being within the scope of the present invention.

Preferably, the protrusions extend at least 0.002 inches so that they can sufficiently grip into patient tissue (analogous to a knobby tire gripping soft dirt). The protrusions 106 can extend radially from the therapeutic member 100. For example, in the embodiments shown, the protrusions 106 extend in directions that are generally perpendicular to the longitudinal axis 103 of the therapeutic member 100 and the source (e.g., seed) 102 therein. The protrusions 106 may alternatively or additionally extend at other angles with respect to the longitudinal axis 103. For example, protrusions may extend at 45 degrees with respect to the longitudinal axis 103. In a specific embodiment, each half of the member 100 can have protrusions 106 at a 45 degree angle facing towards the middle of the member 100, or towards the ends of the member 100. Various other angles, and combinations of angles, are also possible.

In FIGS. 1A and 1B, and FIGS. 2-5 discussed below, the protrusions are shown as extending from the length of the therapeutic member. However, the protrusions may also extend from the longitudinal ends of the therapeutic member.

Figure 2:
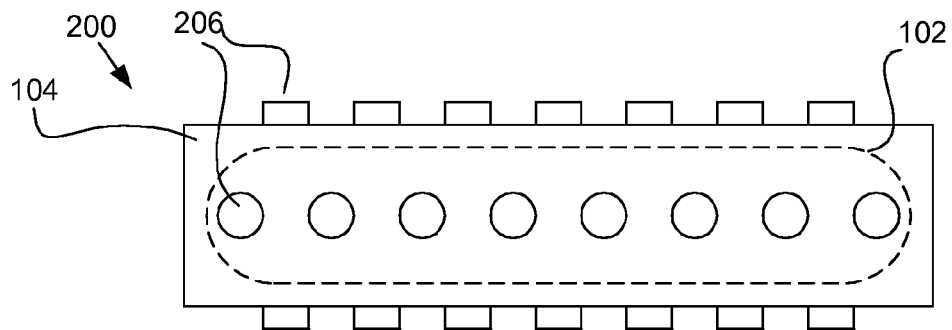
FIGS. 2-5 are side views of therapeutic members according to various embodiments of the present invention.
Figure 3:
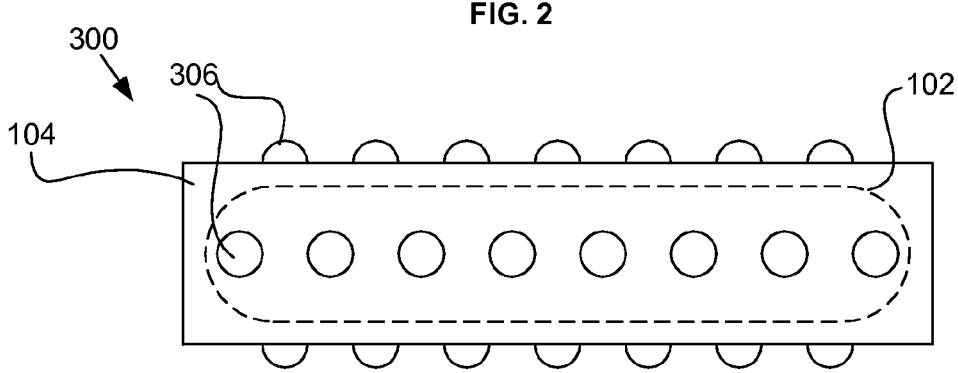
Figure 4:
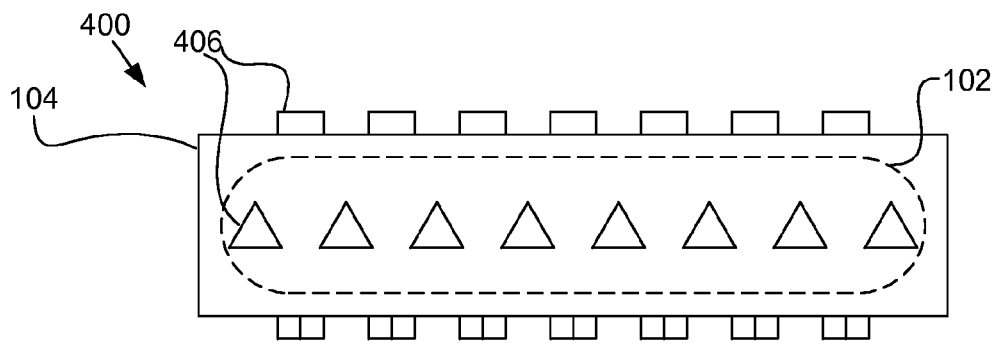

In another embodiment, shown in FIG. 2, the protrusions 206 of a therapeutic member 200 are cylindrical. In still another embodiment, shown in FIG. 3, a therapeutic member 300 includes protrusions 306 that resemble bumps or semispheres. In the embodiment shown in FIG. 4 the protrusions 406 of a therapeutic member 400 are triangular, and in the embodiment of FIG. 5 the protrusions 506 of a therapeutic member 500 are pyramidal. These are just a few examples of the shapes of the protrusions. One of ordinary skill in the art reading this description would appreciate that other shapes are also possible. It should also be understood that a therapeutic member of the present invention can include protrusions of numerous different shapes, including, but not limited to, the shapes shown in FIGS. 1-5. While in the FIGS. the various protrusions are shown as having a common orientation, it is also within the scope of the present invention that the protrusions have different orientations. For example, in FIG. 5, different triangular protrusions 506 can have different orientations.

Figure 6A:
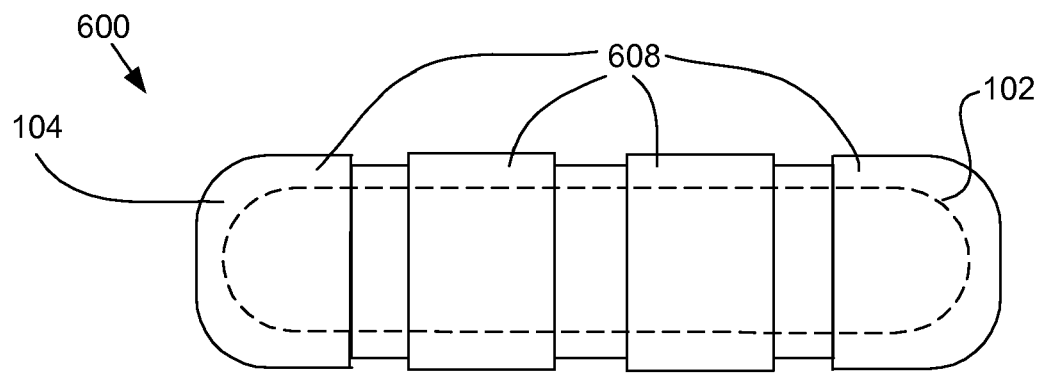
FIG. 6A is a side view of a therapeutic member according to a further embodiment of the present invention.
Figure 6B:
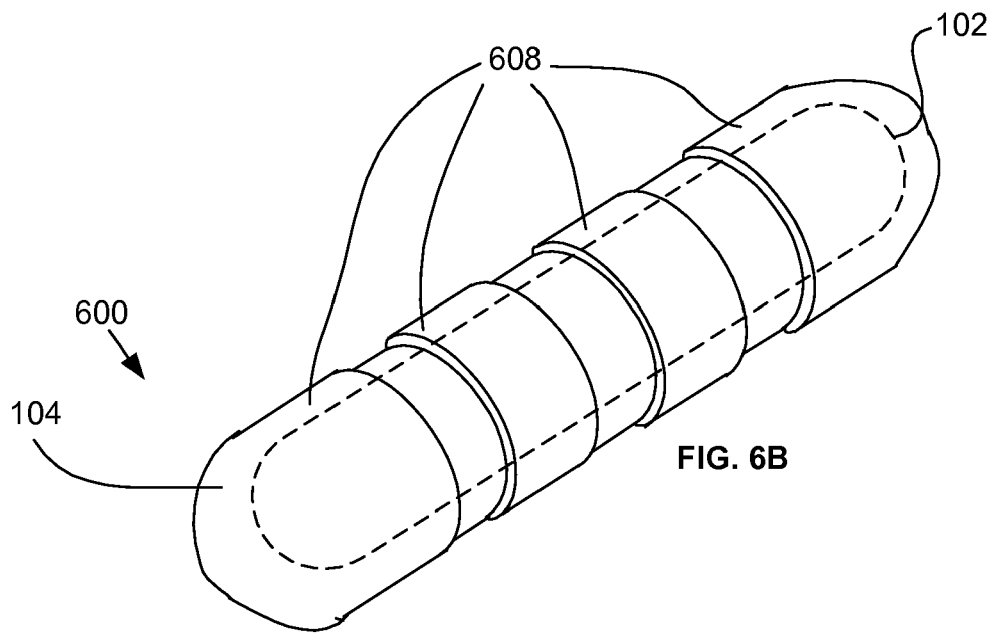
FIG. 6B is a perspective view of the therapeutic member shown in FIG. 6A.

In a further embodiment, shown in FIGS. 6A and 6B, the protrusions are ribs 608 that encircle the underlying source 102. Four ribs 608 are shown in FIGS. 6A and 6B. However, it should be understood that more or less ribs 608 can be included. It should also be understood the ribs can be helical (i.e., spiral). In one specific embodiment, the ribs can form counter balancing screw threads (i.e., opposing helixes). For example, the threads on one half of the member can be right hand threads, while the threads on the other half of the member can be left hand threads.

In the embodiments where the radioactive sources 102 are radioactive seeds, the seeds 102 can be of various types having low energy and low half-life such as Iodine seeds, known as I-125 seeds, including a welded titanium capsule containing iodine 125 adsorbed on a silver rod, or Palladium 103 seeds. Seeds may also have there isotope adsorbed on ceramic beads, resin beads, silver beads, graphite pellets, porous ceramic rods, copper cores, etc. Seed can have various different shapes, such as, but not limited to, cylindrical with flat ends, cylindrical with rounded (e.g., bullet shaped) and spherical. Exemplary dimensions of a seed 102 are 0.18 inches in length and 0.0315 inches in diameter. Exemplary seeds are listed below in Table 1, but embodiments of the present invention should not be limited to the seeds listed therein.

TABLE 1

Seed Manufacturers and Common Types of Seeds

| MANUFACTURER | SEED NAME |
|---|---|
| IODINE$^{125}$ | |
| Amersham 6711 | ONCOSEED ® |
| Amersham 6733 | ECHOSEED ® |
| Amersham 7000 | RAPID STRAND ® |
| North American Scientific | IOGOLD ™ |
| Best Industries | BEST IODINE-125 ™ |
| Bebig | SYMMETRA ™ |
| Mills Biopharmaceuticals | PROSTASEED ™ |
| Syncor | PHARMASEED ™ |
| International Isotopes | ISOSTAR ™ |
| Implant Sciences | I-PLANT ™ |
| International Brachytherapy | INTERSOURCE-125 ® |
| IsoAid | ADVANTAGE I-125 ® |
| Source Tech | STM1251 ™ |
| DRAXIMAGE, Inc. | BRACHYSEED ® |
| PALLADIUM$^{103}$ | |
| North American Scientific | PD GOLD ™ |
| Theragenics | THERASEED 200 ® |
| Best Industries | BEST PALLADIUM-103 ™ |
| International Brachytherapy | INTERSOURCE 103 ® |

Alternatively, seeds 102 can be manufactured using iridium 192, cesium 131, gold 198, yttrium 90 and/or phosphorus 32. Further radioactive isotopes used to manufacture seeds are not limited to these examples, but can include other sources of different types of radiation.

In addition it is to be understood that other types of seeds can be used. For example, seeds such as those described in U.S. Pat. No. 6,248,057, which is incorporated herein by reference, can be used with the present invention. These seeds include radiation delivery devices, drug delivery devices, and combinations of radiation and drug delivery devices in the form of beads, seeds, particles, rods, gels, and the like. These particular seeds are absorbable wherein the radiation member or drug delivery member is contained within, for example, absorbable polymers such as those listed below or in the above-referenced patent. In such seeds, the bioabsorbable structure can have a predefined persistence which is the same as or substantially longer than a half life of the radioactive member contained in the bioabsorbable structure. These above bioabsorbable seeds can be used in the same manner as the seeds described herein with respect to the invention. As mentioned above, the radioactive sources 102 need not be seeds. For example, the radioactive sources 102 can be rods, e.g., metallic rods coated with a radioactive isotope such as palladium 103, etc. The radioactive sources 102 may also be radioactive coils, such as those described in U.S. Pat. No. 6,419,621, which is incorporated herein by reference, and those available from RadioMed Corporation of Tyngsboro, Mass., under the trademarks GENETRA™ and RADIO COIL™. In accordance with an alternative embodiment, rather than using a radioactive source, an implant that utilizes thermal ablation to treat cancer can be used. One such implant, which is marketed under the trademark THERMOROD™, and is available from Ablation Technologies of San Diego, Calif., is a permanently implantable cobalt-palladium alloy rod that produces heat (e.g., 70 degrees C.) through oscillation of a magnetic field. In such embodiments, the material 104 is used to encapsulate the thermal ablation implant and to form protrusions, as described above, to resist migration and rotation of the implant.

To allow X-ray detection of the radioactive sources, the radioactive sources can include a radiopaque marker, which is typically made of a dense, high atomic number material, such as gold or tungsten, which can block the transmission of X-rays so that the radioactive source can be detected by using X-ray imaging techniques. This can be accomplished, e.g., by including a ball, rod or wire constructed of a dense, high atomic number material, such as gold or tungsten, within the container of a radioactive source (e.g., seed). Alternatively, the radioactive seed (or other source) can be at least partially coated with a radiopaque material.

The therapeutic members of the present invention can be manufactured in various manners. For example, a molding process, such as compression molding or injection molding can be used. In one example, a radioactive source is placed into an embossing mold that includes the inverse (i.e., negative) of the pattern of projections that is to be embossed on the outer surface of the polymeric material. Before or after the source (e.g., seed) is placed in the mold, a bioabsorbable polymer or some other plastic material is introduced into the mold at a temperature that is above the melt point of the material such that the material flows around the seed within the mold cavity. The material is then allowed to set within the mold, e.g., by cooling the mold. After the material has set, the mold is opened, and the finished therapeutic member with a plurality of polymeric projections is removed. In other embodiments, an encapsulating material is molded around the seed, and then the protrusions are produced in a secondary process, e.g., by machining, crimping or otherwise altering the shape of the encapsulating material to form protrusions. In still other embodiments, the protrusions are formed in the encapsulating material prior to the seed being placed into the material. In still further embodiments, the protrusions can be doughnut shaped pieces that are slid over the radioactive source implant. These are just a few examples. Other techniques for producing the protrusions are also within the scope of the present invention.

Figure 7A:
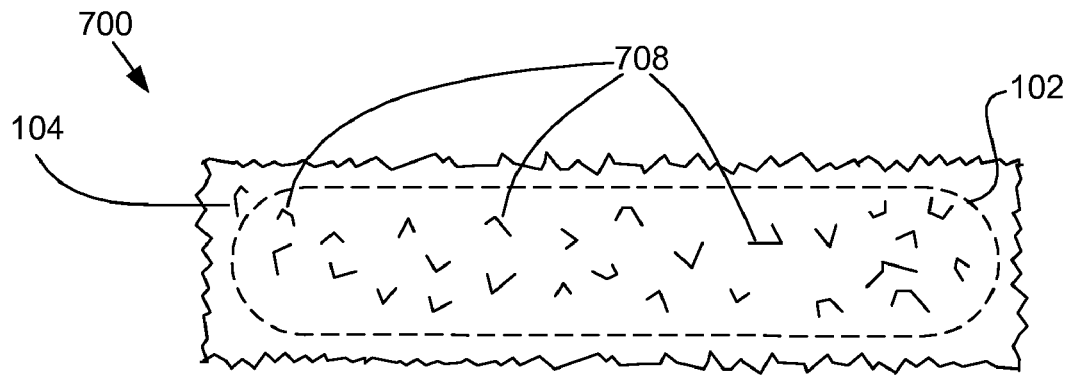
FIG. 7A is a side view of a therapeutic member according to another embodiment of the present invention.
Figure 7B:
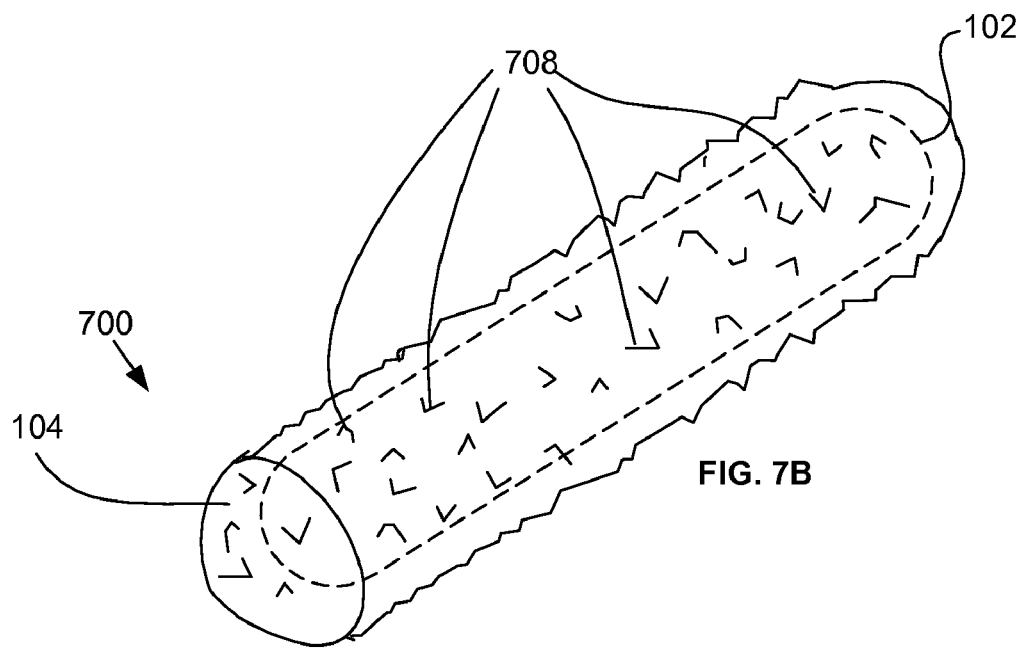
FIG. 7B is a perspective view of the therapeutic member shown in FIG. 7A.

In another embodiment, the plurality of protrusions can form an irregular pattern on the outer surface of the encapsulating polymeric material 104. For example, the protrusions can form what resembles a rough stucco like surface, e.g., as shown in FIGS. 7A and 7B. For the embodiment of FIGS. 7A and 7B, where the outer surface or the member 700 resembles a rough stucco surface, a mold can include purposeful protrusions, or can simply be a rough surface that was formed when casting or otherwise manufacturing the mold. Typically, the metal of the mold would be machined such that a member produced using the mold would have a generally smooth surface. However, in accordance with an embodiment of the present invention the mold is left rough, so that the member 700 formed using the mold would have random protrusions.

In another embodiment, a radioactive source 102 is encapsulated within a polymeric material, and then protrusions are attached to the outer surface of the encapsulating material in a secondary process. For example, while the outer surface of the encapsulating material is tacky, particles or strands can be attached to the outer surface to thereby form the protrusions. The outer surface of the encapsulating material can be made tacky by heating the material, coating the material with a biocompatible adhesive, or otherwise wetting the material. The particles or strands can then be attached to the outer surface of the material, e.g., by sprinkling the particles or strands onto the outer surface, or rolling the encapsulated source in the particle or strands. Such particles or strands should be biocompatible, and can also bioabsorbable. The particle or strands can be made of the same material as the material 104 that encapsulates the radioactive source 102, but this is not necessary. It is also possible that the container of the radioactive source be coated with a biocompatible adhesive, and that the particles or strands are directly attached to the container of the radioactive source, to thereby form the protrusions that resist migration and rotation.

Figure 8A:
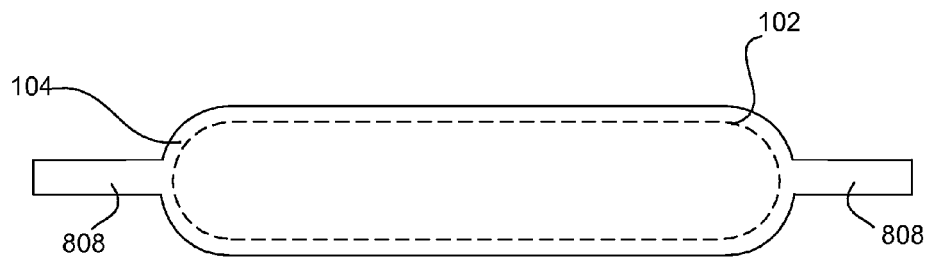
FIG. 8A is a side view of a member with tabs.
Figure 8B:
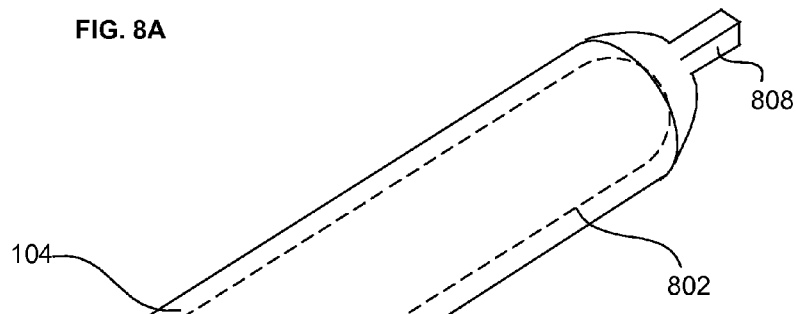
FIG. 8B is a perspective view of the member shown in FIG. 8A.
Figure 8C:
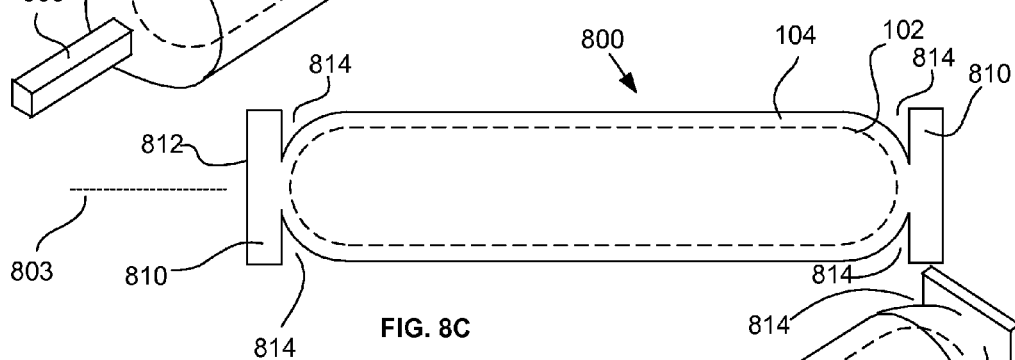
FIG. 8C is a side view of the therapeutic member of FIGS. 8A and 8B after the tabs have been shaped into anchor mechanisms.
Figures 8D, 8E:
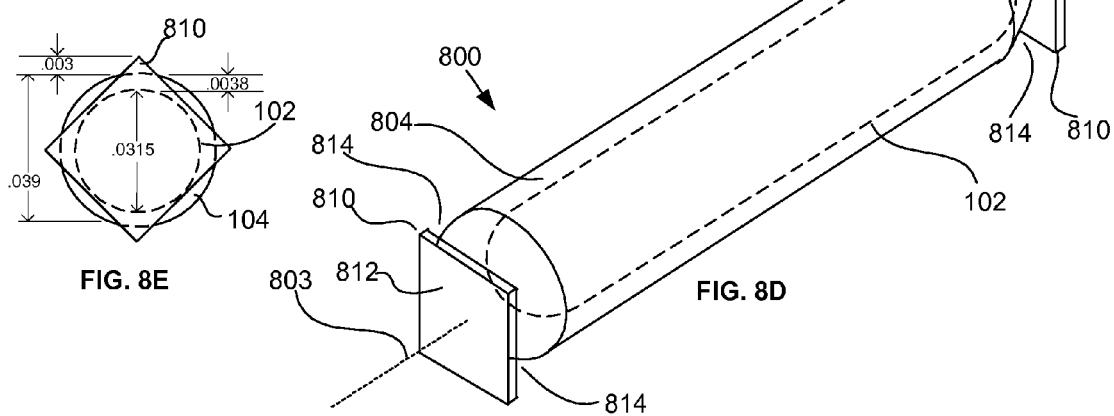
FIG. 8D is a perspective view of the member shown in FIG. 8C.
FIG. 8E is an end view of the therapeutic member shown in FIGS. 8C and 8D.

In another embodiment, the material 104 can be molded or otherwise formed around a source 102 such that a tab 808 extends longitudinally (i.e., axially) from each longitudinal end of the encapsulated radioactive source 102, as shown in FIGS. 8A and 8B. In a secondary process, each tab 808 is heated and formed into an anchor mechanism 810, shown in FIGS. 8C and 8D. More specifically, the main body of the member 800 (within which the seed 102 is located) can be held in place while each tab 808 is melted into a desired shape by pushing against the tab 808 with a heated surface or mold that is moved toward the main body of the member. The heated surface or mold that is used to melt the tab 808 can simply be a flat surface, which will cause the anchor mechanism 810 to have an amorphous shape. Alternatively, the mold that is used to melt the tab 808 can be shaped to cause the anchor mechanism 810 to have a specific shape, such as a square, as shown in FIGS. 8C and 8D. FIG. 8E, which is an end view of the member 800 shown in FIGS. 8C and 8D, includes exemplary dimensions in inches.

In FIGS. 8C-8E, the anchor mechanism 810 is square shaped. In alternative embodiments the anchor mechanisms can have other shapes. For example, the anchor mechanism 810 can be amorphous, rectangular, triangular, trapezoidal, etc. In accordance with specific embodiments, an outer surface 812 of the anchor mechanism 810 is generally perpendicular to the longitudinal axis 103 of the radioactive source 102, as shown in FIGS. 8C and 8D. A void or groove 814 is formed between the main portion of the member and the anchor mechanism 810, thereby allowing patient tissue to occupy this void 814 to reduce the tendency for the member 800, and the radioactive source 102 therein, to migrate or rotate.

It is preferred that the anchor mechanism 810 be located at each longitudinal end of the therapeutic member 800, as shown in FIGS. 8C and 8D. However, in alternative embodiments the anchor mechanism 810 can be located at only one of the longitudinal ends of the member. In FIGS. 8A-8E the outer surface of the main body of the therapeutic member 800 is shown as being generally cylindrical and smooth. However, this need not be the case. The embodiments of FIGS. 1-7 discussed above can be combined with the embodiments of FIGS. 8A-8E. For example, a same mold that is used to form the protrusions of FIGS. 1-7 can be used to form the tabs 808, which can then shaped into the anchor mechanisms 810 in a secondary process after the members have been removed from the mold. In still another embodiment, the anchor mechanisms 810 can be formed by an embossing mold similar to that used to form the protrusions of FIGS. 1-7.

The radioactive sources 102 can be coated with or contain a drug and/or hormone. Alternatively, a drug and/or hormone can be included in the encapsulating material 104 that is used for form the protrusions or anchor mechanisms of the present invention.

Example types of materials 104 that are bioabsorbable include, but are not limited to, synthetic polymers and copolymers of glycolide and lactide, polydioxanone and the like. Such polymeric materials are more fully described in U.S. Pat. Nos. 3,565,869, 3,636,956, 4,052,988 and European Patent Publication No. 0030822, all of which are incorporated herein by reference. Specific examples of bioabsorbable polymeric materials that can be used to produce the therapeutic members of embodiments of the present invention are polymers made by Ethicon, Inc., of Somerville, N.J., under the trademarks MONOCRYL® (polyglycoprone 25), MAXON® (Glycolide and Trimethylene Carbonate), VICRYL® (polyglactin 910) and PDS II™ (polydioxanone).

Other exemplary bioabsorbable materials include poly(glycolic acid) (PGA) and poly(-L-lactic acid) (PLLA), polyester amides of glycolic or lactic acids such as polymers and copolymers of glycolate and lactate, polydioxanone and the like, or combinations thereof. Such materials are more fully described in U.S. Pat. No. 5,460,592 which is hereby incorporated by reference. Further exemplary bioabsorbable polymers and polymer compositions that can be used in this invention are described in the following patents which are hereby incorporated by reference: U.S. Pat. No. 4,052,988 which discloses compositions comprising extruded and oriented filaments of polymers of p-dioxanone and 1,4-dioxepan-2-one; U.S. Pat. No. 3,839,297 which discloses compositions comprising poly[L(-)lactide-co-glycolide] suitable for use as absorbable sutures; U.S. Pat. No. 3,297,033 which discloses the use of compositions comprising polyglycolide homopolymers as absorbable sutures; U.S. Pat. No. 2,668,162 which discloses compositions comprising high molecular weight polymers of glycolide with lactide; U.S. Pat. No. 2,703,316 which discloses compositions comprising polymers of lactide and copolymers of lactide with glycolide; U.S. Pat. No. 2,758,987 which discloses compositions comprising optically active homopolymers of L(-) lactide i.e. poly L-Lactide; U.S. Pat. No. 3,636,956 which discloses compositions of copolymers of L(-) lactide and glycolide having utility as absorbable sutures; U.S. Pat. No. 4,141,087 which discloses synthetic absorbable crystalline isomorphic copolyoxylate polymers derived from mixtures of cyclic and linear diols; U.S. Pat. No. 4,441,496 which discloses copolymers of p-dioxanone and 2,5-morpholinediones; U.S. Pat. No. 4,452,973 which discloses poly(glycolic acid)/poly(oxyalkylene) ABA triblock copolymers; U.S. Pat. No. 4,510,295 which discloses polyesters of substituted benzoic acid, dihydric alcohols, and glycolide and/or lactide; U.S. Pat. No. 4,612,923 which discloses surgical devices fabricated from synthetic absorbable polymer containing absorbable glass filler; U.S. Pat. No. 4,646,741 which discloses a surgical fastener comprising a blend of copolymers of lactide, glycolide, and poly(p-dioxanone); U.S. Pat. No. 4,741,337 which discloses a surgical fastener made from a glycolide-rich blend of polymers; U.S. Pat. No. 4,916,209 which discloses bioabsorbable semi-crystalline depsipeptide polymers; U.S. Pat. No. 5,264,540 which discloses bioabsorbable aromatic polyanhydride polymers; and U.S. Pat. No. 4,689,424 which discloses radiation sterilizable absorbable polymers of dihydric alcohols. If desired, to further increase the mechanical stiffness of the molded embodiments of the present invention, bioabsorbable polymers and polymer compositions can include bioabsorbable fillers, such as those described in U.S. Pat. No. 4,473,670 (which is incorporated by reference) which discloses a composition of a bioabsorbable polymer and a filler comprising a poly(succinimide); and U.S. Pat. No. 5,521,280 (which is incorporated by reference) which discloses bioabsorbable polymers and a filler of finely divided sodium chloride or potassium chloride.

The final hardness of a polymer of the therapeutic members of the present invention should preferably be in a range from 20 to 80 durometer and more preferably in the range of 20-40 durometer. However, members with other hardnesses are also within the scope of the present invention. Where the material 104 is bioabsorbable, the bioabsorbable material should preferably be absorbed in living tissue in a period of time of from about 70 to about 120 days, but can be manufactured to be absorbed anywhere in a range from 1 week to 1 year or more, depending on the therapeutic plan for a specific patient. The material 104 should also be biocompatible, whether or not it is bioabsorbable. The material 104 may also be bio-adhesive.

In accordance with an embodiment of the present invention, the minimum thickness of the material 104 that encapsulates the source 102 should be about 0.002 inches. Such minimum thickness would occur at locations where there is not a protrusion. The preferred thickness of the material 104 where there is not a protrusion is about 0.004 inches. As mentioned above, the protrusions preferably extend at least 0.002 inches so that they can sufficiently grip into patient tissue. Such extension of the protrusions is that which is beyond the underlying thickness of the material 104. The protrusions are preferably separated from one another a sufficient distance such that the voids formed between the protrusions allow patient tissue to occupy these voids to reduce the tendency for the therapeutic member, and the radioactive source 102 therein, to migrate or rotate. Preferably, these voids or spaces between protrusions are at least 0.010 inches, so that patient tissue can fit into these spaces. The overall dimensions of the therapeutic members of the present invention are limited by the inner diameter of the needle that is to be used to implant the members. For example, the larger the inner diameter of the needle, the more the protrusions can extend.

The term polymer, as used herein, is also meant to include copolymers. Table 2 below provides examples of bioabsorbable polymers suitable for use in producing embodiments of the present invention, along with specific characteristics (e.g., melting points) of the various polymers. A further discussion of such bioabsorbable polymers can be found in an article by John C. Middleton and Arthur J. Tipton entitled "Synthetic Biodegradable Polymers as Medical Devices," published March 1998 in Medical Plastics and Bio-materials, which article is incorporated herein by reference.

TABLE 2

Biodegradable polymers, properties and degradation time

| POLYMER | MELTING POINT (° C.) | GLASS-TRANSITION TEMP (° C.) | MODULUS Gpa$^a$ | DEGRADATION TIME (MONTHS)$^b$ |
|---|---|---|---|---|
| PGA | 225-230 | 35-40 | 7.0 | 6 to 12 |
| LPLA | 173-178 | 60-65 | 2.7 | >24 |
| DLPLA | Amorphous | 55-60 | 1.9 | 12 to 16 |
| PCL | 58-63 | (−65)-(−60) | 0.4 | >24 |
| PDO | N/A | (−10)-0 | 1.5 | 6 to 12 |
| PGA-TMC | N/A | N/A | 2.4 | 6 to 12 |
| 85/15 DLPLG | Amorphous | 50-55 | 2.0 | 5 to 6 |

TABLE 2-continued

Biodegradable polymers, properties and degradation time

| POLYMER | MELTING POINT (° C.) | GLASS-TRANSITION TEMP (° C.) | MODULUS Gpa[a] | DEGRADATION TIME (MONTHS)[b] |
|---|---|---|---|---|
| 75/25 DLPLG | Amorphous | 50-55 | 2.0 | 4 to 5 |
| 65/35 DLPLG | Amorphous | 45-50 | 2.0 | 3 to 4 |
| 50/50 DLPLG | Amorphous | 45-50 | 2.0 | 1 to 2 |

[a]Tensile or flexural modulus.
[b]Time to complete mass loss. Rate also depends on part geometry.

Figure 9:
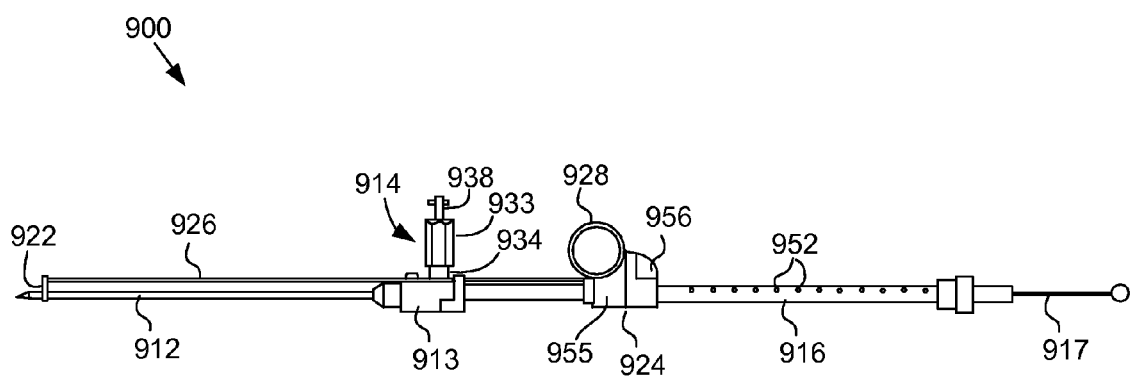
FIG. 9 is a side view of an exemplary applicator that can be used to implant therapeutic members of the present invention into a patient's body.

FIG. 9 illustrates an exemplary applicator 900, often referred to as a MICK® applicator, that can be used to implant the therapeutic members of the present invention at variable spaced locations within a patient's body. Such an applicator 900 is available from Mick Radio-Nuclear Instruments, Inc., of Mount Vernon, N.Y.

The applicator 900 includes a hollow needle 912 insertable into the patient's body, a needle chuck 913 for releasably holding the needle 912, a magazine 914 for holding and dispensing therapeutic members of the present invention (containing seeds or other radioactive sources) into the needle chuck 913, a main barrel 916 connected to the needle chuck 913. Also shown in FIG. 9 is a stylet 917 extendable through the main barrel 916, the needle chuck 913, and a bore of the needle 912. The applicator 900 also includes a base frame member along which the needle 912, the needle chuck 913, the magazine 914 and the main barrel 916 are slidably mounted. The frame member includes an abutment end 922 adapted to abut a surface of the patient's body or a template (not shown) fixed with respect to the body, a barrel collar 924 through which the main barrel 916 is slidable, and two rods 926 (only one can be seen in the side view of FIG. 9) extending between and fixedly attached to the abutment end 922 and the collar 924. The collar 924 is equipped with a finger ring 928 for receiving a finger of a user.

The applicator 900 is designed to allow the needle 912 to be moved in different increments with respect to the base frame. For this purpose, the main barrel 916 includes rows of detents or indentations 952 that extend along the length of the barrel 916, with each row having different indentation spacing (only one row is shown in FIG. 9) For example, the applicator 900 can have a first row of indentations spaced at 3.75 mm, a second row of indentations spaced at 4.0 mm, a third row of indentations spaced at 5.0 mm, a fourth row of indentations spaced at 5.5 mm, and a fifth row of indentations at 6.0 mm. These spacings can be changed as desired by using an applicator having a main barrel with other indentation spacings.

The barrel collar 924 includes a fixed portion 955 and a spacing dial 956 rotatably mounted on the fixed portion 955. An operator can turn the dial 956 relative to the fixed portion 955 to select one of the rows or series of indentations.

The magazine 914 includes a magazine head 933 and a cartridge 934 in which therapeutic members of the present invention can be stacked parallel to each other. A spring-loaded magazine plunger 938 is biased against the therapeutic members (each of which includes a radioactive source 102) at the upper end of the magazine 914 to facilitate movement of the therapeutic members into the needle chuck 913 and to provide an indication to the operator that a therapeutic member has been dispensed from the cartridge 934.

The cartridge 934 can be preloaded with a plurality of therapeutic members of the present invention (e.g., up to 20 members, each with a radioactive source 102) and then screwed into the magazine head 933. The cartridge 934 can be keyed to the needle chuck 913 to prevent its incorrect insertion into the needle chuck 913.

In the operation, the needle 912 is inserted into a patient in an area where a single radioactive source or row of radioactive sources is to be implanted. Then, the needle chuck 913 of the body of the applicator 900 is coupled with the protruding end of the needle 912 to prepare the applicator 900 for use. An initial radioactive source spacing can be set by adjusting the spacing dial 956 to select a particular row of indentations 952 on the main barrel 916 corresponding to the desired spacing. The stylet 917, which is initially fully extended in the needle 912, is then retracted from the needle 912 and the needle chuck 913, enabling a therapeutic member (including a radioactive source) from the magazine 914 to be positioned in the chuck 913 for movement into the needle 912. When the style 917 is retracted, the therapeutic member is moved into the chuck and the extended magazine plunger 938 will move further into the magazine 914, which will indicate to the operator that a member has been positioned for transfer into the needle 912. The stylet 917 is then pushed through the barrel 916 against the therapeutic member, forcing the member through the needle 912 and into the patient's body.

After a first member (including a radioactive source) has been implanted, the needle 912 is withdrawn from the patient's body by a particular distance so that the next radioactive source to be implanted is spaced apart from the first radioactive source. Then, the stylet 917 is again retracted to enable the next therapeutic member (with a radioactive source) from the magazine 914 to be positioned for movement into the needle 912. The stylet 917 is then advanced through the needle 912 to force the therapeutic member into the patient's body at a desired distance away from the first member. This procedure is repeated for subsequent therapeutic member implants. Additional details of this process and the applicator 900 can be found in U.S. Pat. No. 5,860,909, which is incorporated herein by reference. This is just one example of a device that can be used to implant therapeutic members of the present invention. Other devices may also be used, while still being within the scope of the present invention. For example, rather than using cartridges as described above, therapeutic members of the present invention (and optionally, spacers therebetween) can be preloaded into a needle that is used to implant a row of such members (and optionally, spacers therebetween) in a single needle track.

The conventional stylet 917 that is used with an applicator, such as a MICK® applicator, is made using a solid wire. However, this can result in the mislocation of the sources in the needle track due to vacuum phenomena occurring as the needle and stylet are withdrawn. To overcome this problem, the stylet 917 is preferably a vented stylet that includes a vent that extends the length of the stylet, as described in U.S. Pat. No. 6,554,760, which is incorporated herein by reference.

Embodiments of the present invention, as described above, are directed to therapeutic members that include protrusions and/or anchor mechanisms that reduce the tendency for the therapeutic member and the radioactive source therein to migrate and rotate within a patient's body after implantation. Embodiments of the present invention are also directed to cartridges, similar to 934, that are pre-loaded with such therapeutic members.

The above mentioned embodiments of the present invention relate to therapeutic members that include a single radioactive source (a single seed, rod or coil). It is also possible that embodiments of the present invention can be used together with elongated members known as strands that include multiple radioactive sources that are spaced from one another, e.g., as described in U.S. patent application Ser. No. 10/035,083, which was filed on Dec. 28, 2001, and which is incorporated herein by reference. More specifically, one or more therapeutic member as described in FIGS. 1-7, which each include a single radioactive source 102, can be used together with one or more strand that includes multiple radioactive sources.

For example, a single needle can be loaded with a therapeutic member having a single radioactive source as well as with a strand having multiple radioactive sources, thereby allowing for implantation of both during the same procedure that include insertion and removal of the needle. This would be useful, e.g., where a first radioactive source in a row of radioactive sources is to be located near a patient's bladder or urethra. If a strand of radioactive sources were being implanted, and the end of the strand were inserted too far and into the patient causing it to enter the bladder or urethra, then the entire strand would have to be removed from the patient. However, if the first radioactive source implanted was within a therapeutic member of the present invention, and that radioactive source got into the bladder or urethra, then it would be possible to remove the single first radioactive source without removing strand that followed the first radioactive source.

As mentioned above, seeds (or other radioactive sources) are sometimes implanted into a patient by preloading a hollow needle with seeds and spacers that are used to maintain a desired distance between a row of seeds, e.g., as described in U.S. Pat. No. 6,554,760, which is incorporated herein by reference. The seeds and spacers are deployed from the hollow needle using a stylet, which preferably includes a radial vent that extends the length of the stylet, to reduce the mislocation of the radioactive sources in the needle track due to vacuum phenomena occurring as the needle and stylet are withdrawn. In such implants, the first and last seeds are the most likely seeds to migrate and/or rotate, however the other seeds, as well as the spacers, may also migrate and/or rotate within the needle track. To reduce migration of the seeds, therapeutic members of the present invention can be used. That is, a seed can be encapsulated by a material that includes protrusions that will resist the migration and rotation of the seed therein. In another embodiment, protrusions can be added to the spacers that are used to maintain the desired distances between the radioactive sources. Such spacers with protrusions can be made in manners similar to those explained above. For example, protrusions can be added to preexisting spacers (e.g., cylindrical spacers) by encapsulating the spacer with a material within which protrusions are formed. Alternatively, spacers can be manufactured to include protrusions. Such spacers can be formed, e.g., using an embossing mold, or by machining, crimping or otherwise forming protrusions in an outer surface of the spacers. The spacers with protrusions can be used together with therapeutic members having protrusions, or with radioactive sources that do not have protrusions. When used with radioactive sources not having protrusions, the spacers with protrusions would preferably be located at both longitudinal ends of the radioactive sources, to thereby trap the radioactive sources in place. For example, if five radioactive seeds were to be implanted in a single needle track, six such spacers can be used (i.e., four spacers each of which separate pairs of seeds, and a spacer prior to the first seed, and a spacer following the last seed). The spacers that are located between seeds preferably include protrusions similar to those explained with reference to FIGS. 1-7. The spacers that are located prior to the first seed and following the last seed in the needle track can include protrusions similar to those explained with reference to FIGS. 1-7, or can include anchor mechanisms similar to those described above with reference to FIGS. 8A-8D. The spacers with protrusions can be made entirely from a bioabsorbable material, examples of which are listed above. Alternatively, the spacers with protrusions can be made from a non-bioabsorbable material which is biocompatible. In still another embodiment, the spacer is made of a body that is biocompatible but non-bioabsorbable, which is encapsulated within a bioabsorbable material that is used to form the protrusions.

FIGS. 10A-10C illustrate a spacer 1000 according to another embodiment of the present invention. As shown in FIGS. 10A-10C, the spacer 1000 includes two halves 1002 and 1004 that are connected by a living hinge 1006. The halves 1002 and 1004 are shown as being half cylinders, but other shapes are also possible. The living hinge 1006 is biased such that after the spacer is folded into its closed position (FIG. 10B), the spacer tends to open up such that a gap 1008 forms between the two halves (FIG. 10C). This can be accomplished, e.g., by molding the two halves 1002 and 1004 and the living hinge 1006 in the open position shown in FIG. 10A. The two haves 1002 and 1004 can then be folded toward one another along the living hinge 1006 to place the spacer 1000 in the closed position shown in FIG. 10B, at which point the spacer can be inserted into a hollow needle used to implant spacers and radioactive sources in a patient. Once implanted in the patient, the spacer 1000 will tend to open or unfold along the living hinge 1006, causing an outer surface of the spacer 1000 to thereby engage the patient tissue that surrounds the spacer 1000. This engagement with patient tissue will cause the spacer to resist migration and rotation. To further resist migration and rotation, protrusions, such as those discussed above, can be added to the outer surface of the spacer. The spacer 1000 can be made entirely from a bioabsorbable material, examples of which are listed above. Alternatively, the spacer 1000 can be made from a non-bioabsorbable material which is biocompatible.

Figure 11:
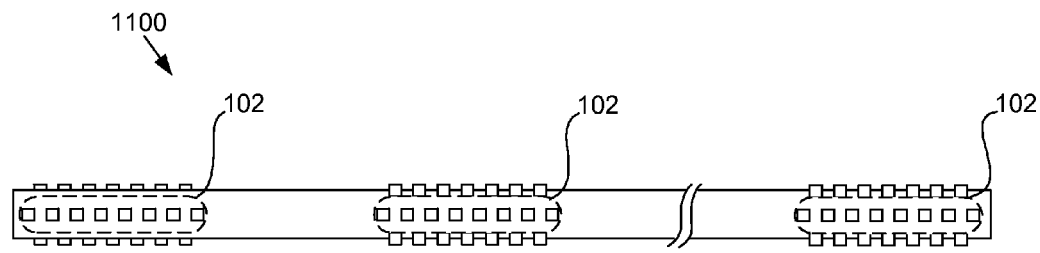
FIG. 11 is a side view of a strand according to an embodiment of the present invention.

In accordance with other embodiments of the present invention, an entire strand 1100 that includes multiple radioactive sources (e.g., seeds) 102, or portions of the strand 1100, can include the protrusions of the present invention, e.g., as shown in FIG. 11. Because a typical strand includes polymeric material that attaches multiple radioactive sources to one another at desired spacings, a strand is not as susceptible to migration and twisting as loose radioactive sources. Nevertheless, it is still possible that that radioactive sources within the strands, especially the radioactive sources located near the distal ends of the strand, can migrate and/or twist. By including protrusions that extend from the strand, the tendency for the strand or portions of the strand to migrate and/or twist can be reduced. Such protrusions can extend from portions of the strand where radioactive sources are located, but can alternatively or additionally extend from other portions of the strand, such as the portions of the strand between the radioactive sources.

Figure 12:
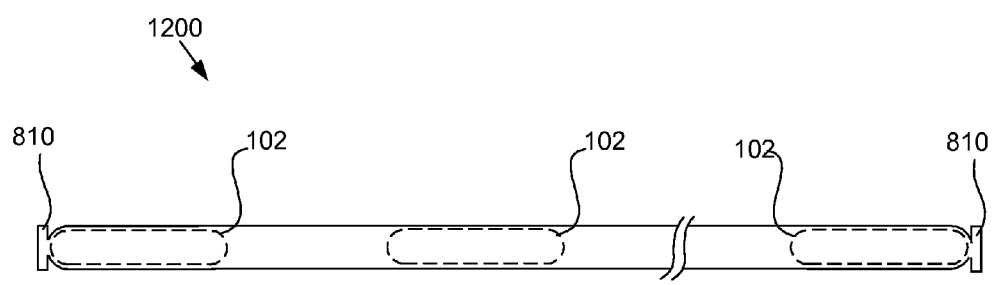
FIG. 12 is a side view of a strand according to another embodiment of the present invention.

In another embodiment of the present invention, the anchor mechanism (e.g., 810) disclosed above with reference to FIGS. 8A-8E can be located at one or both longitudinal distal ends of a strand 1200 that includes multiple radioactive sources 102, e.g., as shown in FIG. 12.

The strands 1100 and 1200 can be manufactured using similar molding processes that were used to produce the therapeutic members of the present invention. For example, to produce the strand 1100, radioactive sources 102 can be placed into an embossing mold that allows the radioactive sources 102 to be spaced at the appropriate intervals in a cavity of the embossing mold that is shaped to the desired final dimensions, including the protrusions, of the strand. All the spacings between the radioactive sources 102 can be of different lengths, if the preoperative therapeutic plan so specifies. Spacers (not shown) can be placed between radioactive sources 102 to keep a desired spacing between the radioactive sources, if desired. Alternative means for maintaining the spacings between adjacent radioactive sources may be used, as is known in the art. The strand 1200 can be manufactured in a similar fashion as was just described, and as was described above with reference to FIGS. 8A-8E.

In accordance with specific embodiments of the present invention, a resulting strand (e.g., 1100 or 1200) is a single solid monofilament of a polymer with the radioactive sources 102 spaced within the monofilament and encapsulated at the appropriate intervals. The strand is preferably axially flexible. However, the strand preferably has sufficient column strength along its longitudinal axis so that the strand can be urged out of a hollow needle without the strand folding upon itself. Again, the intervals can be selected to be any distance or combination of distances that are optimal for the treatment plan of the patient.

In another embodiment, a strand can be made by inserting (i.e., pushing) radioactive sources and spacers through an opening in one end of an elongated hollow tube of bioabsorbable material. Additional details of a seed pusher that can be used in this process are described in U.S. Pat. No. 6,761,680, which was incorporated herein by reference above. The protrusions of the present invention can be formed on the outer surface of the hollow tube prior to or after the insertion of the radioactive sources and spacers.

In a further embodiment, a strand can be constructed using a pair of pre-formed elongated members of bioabsorbable material that are shaped like half-shells, as described in U.S. Pat. No. 6,761,680, which is incorporated herein by reference. The two half-shells can be separate from one another. Alternatively, the two half shells can be connected by a living hinge along their length. The radioactive sources and spacers are placed within a first one of half-shells. The second half-shell is then mated with the first half-shell, and the half-shells are fused together (e.g., using ultrasonic welding or heat), thereby fixing the radioactive sources and spacers inside. The protrusions of the present invention can be formed on the outer surface of such half-shells before or after the radioactive sources and spacers are placed therein.

In still another embodiment, a strand can be made by inserting the seeds and spacers into a tube of braded bioabsorbable material. Additional details of such a braded bioabsorbable tube are described in U.S. Pat. No. 5,460,592, which is incorporated herein by reference. Protrusions can then be added, e.g., by slipping doughnut shaped rings over the breaded material. Such doughnut shaped rings can also be slipped over any other type of strand that has a generally cylindrical outer surface.

Figure 13:
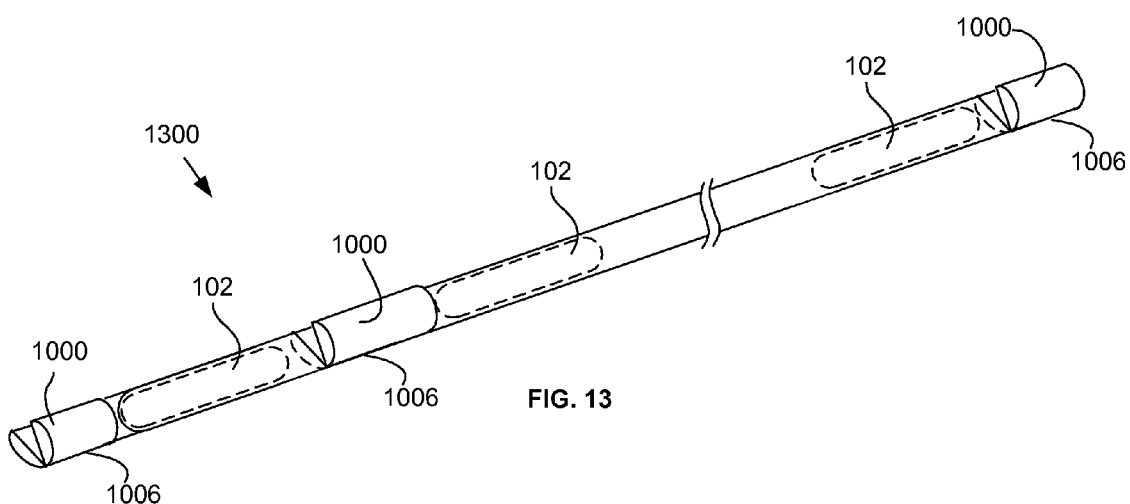
FIG. 13 is a perspective view of a strand that includes portions which are biased to open after implantation, and thereby engage tissue surrounding the strand, to prevent migration and rotation of the strand.

In another embodiment, one or more spacers 1000 that are biased to open (as described above with reference to FIG. 10) can be incorporated into a strand 1300, as shown in FIG. 13. The spacers 1000 can be incorporated into the strand 1300 in various manners, such as by insert molding them into the strand. When the strand 1300 including such spacers 1000 is inserted into a hollow needle, the spacers 1000 will be kept in their closed position by the inner wall of the needle. However, once implanted in a patient, the spacers 1000 will at least partially open and engage the tissue surrounding the spacer, thereby anchoring the entire strand 1300. More generally, portions of the strand 1300 can be biased such that they at least partially open or expand to engage tissue surrounding the strand. As shown in FIG. 13, the portions of the strand that open to engage surrounding tissue can be at one or both distal ends of the strand and/or at locations between the distal ends. In FIG. 13, the living hinges 1006 are shown as being along the length of the strand 1300. However, this need not be the case. For example, a living hinge can be located at one or both of the longitudinal ends of the strand, and thus be perpendicular to the length of the strand.

Embodiments of the present invention are also directed to radiopaque markers that include protrusions and/or anchor mechanisms, similar to those described above, to reduce the tendency of the markers to migrate and rotate within a patient's body after implantation. Such markers can be made entirely or partially of a radiopaque material. Such a radiopaque material is often a dense, high atomic number material, such as gold or tungsten, which can block the transmission of X-rays or other radiation so that the markers can be detected using X-ray or other radiation imaging techniques. For example, a marker can be a ball, rod or wire constructed from gold or tungsten. Alternatively, the marker can be a container that includes a ball, rod or wire of radiopaque material, or a container at least partially coated with a radiopaque material. One commercially available marker is marketed under the trademark VISICOIL® and is available from RadioMed Corporation of Tyngsboro, Mass. These are just a few examples of such markers. One of ordinary skill in the art will understand that other markers are also possible. To add the protrusions and/or anchor mechanisms to an existing marker, the marker can be encapsulated in a polymeric material within which protrusions and/or anchor mechanisms are formed, in any of the manners described above. Alternatively, a marker can be manufactured to include protrusions and/or anchor mechanisms.

The markers can be implanted within a patient that will be undergoing external beam radiation therapy. If the patient is to also undergo brachytherapy, then the markers can implanted at the same time that radiation sources are being implanted into the patient. In specific embodiments, radiopaque markers can be included in spacers and/or strands of the present invention. By including a marker within a spacer or strand that includes protrusions and/or anchor mechanisms, the marker therein will also be resistant to migration and rotation.

In another embodiment, shown in FIGS. 14A-14D, an anchor mechanism 1400 includes a sleeve 1404 to which are attached, by living hinges 1406, wings 1408. The wings 1408 are shown as being generally rectangular, but can have other shapes. Two wings 1408 are shown, but more are less can be used. The sleeve 1404 is intended to be placed around an underlying structure 1402, which can be a radioactive source (e.g., seed, rod or coil), a thermal ablation implant, a spacer, a strand, or a radiopaque marker. Each living hinge 1406 is biased in its open position (FIGS. 14A and 14B), such that after the wings 1408 are folded into their closed positions (FIGS. 14C and 14D), the wings 1408 will tend to open. This can be accomplished, e.g., by molding the anchor mechanism 1400 in the open position shown in FIGS. 14A and 14B. After being placed around an underlying structure 1402, the wings 1408 can then be folded inward along the living hinges 1406 to be in the closed position shown in FIGS. 14C and 14D. When in the closed position, the entire structure, including the underlying structure 1402 and anchor mechanism 1400, can be inserted into a hollow needle used to implant the structure in a patient. The inner wall of the hollow needle will keep the wings 1408 in their closed position. Because of the biasing of the living hinges 1406, once implanted in the patient, the wings 1408 will tend to open or unfold along the living hinges 1406, causing the wings 1408 to thereby engage the surrounding patient tissue. This engagement will resist migration and rotation of the structure 1402. To further resist migration and rotation, protrusions, such as those discussed above, can be added to the wings 1408 and/or sleeve 1404. The anchor mechanism 1400 can be made entirely from a bioabsorbable material, examples of which are listed above. Alternatively, the anchor mechanism can be made from a non-bioabsorbable material which is biocompatible.

Figure 15A:
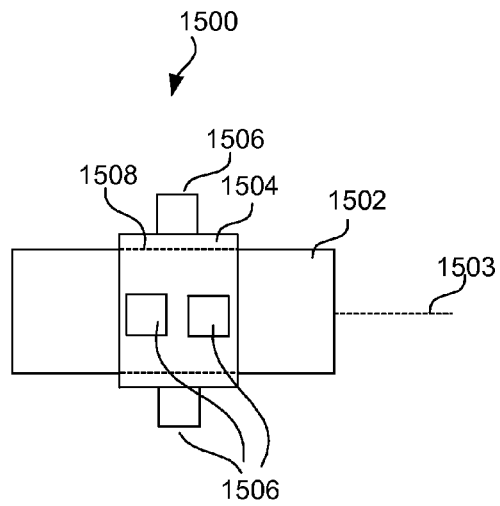
FIG. 15A is a side view illustrating an anchor mechanism according to another embodiment of the present invention.
Figure 15B:
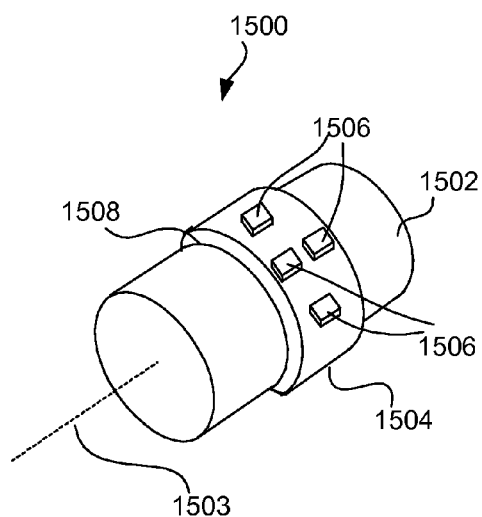
FIG. 15B is a perspective view of the anchor mechanism of FIG. 15A.

In another embodiment, shown in FIGS. 15A-15B, an anchor mechanism 1500 includes a sleeve 1504 from which extends a plurality of protrusions 1506. The sleeve 1504 is intended to be placed around an underlying structure 1502, which can be a radioactive source (e.g., seed, rod or coil), a thermal ablation implant, a spacer, a strand, or a radiopaque marker, prior to implantation of the structure 1502. The protrusions 1506 extending from the sleeve 1504 will reduce a tendency of the underlying structure to migrate and rotate within a patient's body after the structure (with the anchor mechanism 1500 around it) is implanted.

A bore 1508 extends through the anchor mechanism 1500 to form the sleeve 1504. In accordance with specific embodiments of the present invention, the shape of the bore 1508 is generally similar to the shape of the outer diameter of the underlying structure 1502. Thus, if the underlying structure 1502 is a cylindrical radioactive seed, the shape of the bore 1508 is cylindrical, in accordance with specific embodiments.

In accordance with an embodiment, the inner diameter 1508 of the sleeve 1504 (which is the outer diameter of the bore 1508) is sized so that there is an interference fit between the underlying structure 1502 and the sleeve 1504. This can be accomplished by having the inner diameter 1508 of the sleeve 1504 slightly smaller than the outer diameter of the underlying structure 1502. Alternatively, the sleeve 1504 can be heat shrunk to tightly fit around the structure 1502. In another embodiment a biocompatible and preferably bioabsorbable adhesive can be used to secure the sleeve 1504 to the underlying structure 1502. Other mechanisms of securing the sleeve 1504 to the structure 1502 are also within the scope of the present invention. Where the underlying structure 1502 is an elongated strand (e.g., including a plurality of radioactive sources along its longitudinal length), more than one anchor mechanism 1500 can be placed around the strand, e.g., one slightly inward from each longitudinal end of the strand.

The anchor mechanism 1500 can be made entirely from a bio-absorbable material, examples of which are listed above. Alternatively, the anchor mechanism can be made from a non-bio-absorbable material which is bio-compatible.

In FIGS. 15A and 15B the protrusions 1506 are shown as being square or rectangular knobs that cause the outer surface of the anchor mechanism 1500 to resemble a knobby tire. The protrusions 1506 can form a plurality of rows (e.g., four rows) which are regularly spaced about the sleeve 1504, e.g., with each row extending in a direction that is 90 degrees from the adjacent rows. Alternatively, the protrusions can protrude in a more random or irregular fashion.

Exemplary dimensions for one of the protrusions 1506 are 0.010×0.008×0.003 inches. All of the protrusions 1506 can have similar dimensions, or the dimensions of the protrusions may vary. For example, it is possible that the protrusions within a row have similar dimensions, but the dimensions differ for different rows. For a more specific example, another row of protrusions 1506 may have dimensions of 0.006×0.005×0.002 inches. These are just a few examples. One of ordinary skill in the art will appreciate from this description that the protrusions can have other dimensions while being within the scope of the present invention.

Preferably, the protrusions 1506 extend at least 0.002 inches so that they can sufficiently grip into patient tissue (analogous to a knobby tire gripping soft dirt). The protrusions 1506 can extend radially from the sleeve 1504. For example, in the embodiments shown, the protrusions 1506 extend in directions that are generally perpendicular to a longitudinal axis 1503 of the sleeve 1504 and the structure (e.g., seed) 1502 therein. The protrusions 1506 may alternatively or additionally extend at other angles with respect to the longitudinal axis 1503. For example, protrusions may extend at 45 degrees with respect to the longitudinal axis 1503. In a specific embodiment, each half of the sleeve 1504 can have protrusions 1506 at a 45 degree angle facing towards the middle of the sleeve 1504, or towards the ends of the sleeve 1504. Various other angles, and combinations of angles, are also possible.

Figure 5:
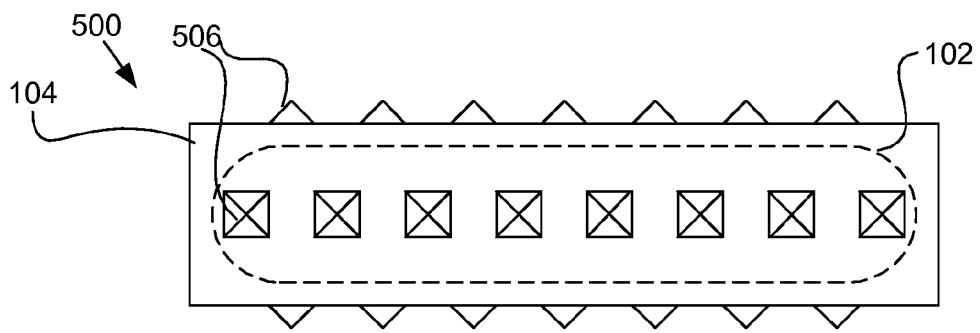

In another embodiment, the protrusions of the anchor mechanism can be cylindrical (e.g., similar to as in FIG. 2), resemble bumps or semi-spheres (e.g., similar to as in FIG. 3), triangular (similar to as in FIG. 4), or pyramidal (similar as in FIG. 5). These are just a few examples of the shapes of the protrusions. One of ordinary skill in the art reading this description would appreciate that other shapes are also possible. It should also be understood that an anchor mechanism of the present invention can include protrusions of numerous different shapes, including, but not limited to, the shapes discussed above. The various protrusions are shown as having a common orientation, but can have different orientations.

Figure 15C:
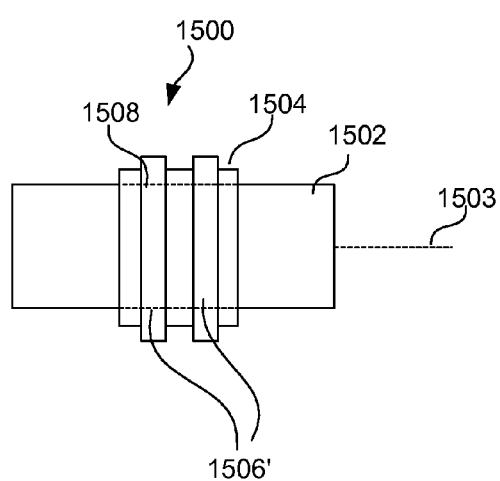
FIG. 15C is a side view illustrating an anchor mechanism according to a further embodiment of the present invention.
Figure 15D:
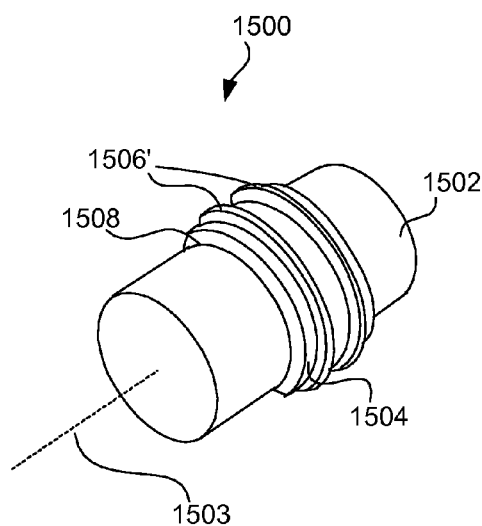
FIG. 15D is a perspective view of the anchor mechanism of FIG. 15C.

In a further embodiment, shown in FIGS. 15C and 15D, the protrusions of the anchor mechanism 1500 are ribs 1506' that encircle the sleeve 1504. Two ribs 1506' are shown in FIGS. 15C and 15D. However, it should be understood that more or less ribs 1506' can be included. It should also be understood the ribs can be helical (i.e., spiral). In one specific embodiment, the ribs can form counter balancing screw threads (i.e., opposing helixes). For example, the threads on one half of the member can be right hand threads, while the threads on the other half of the member can be left hand threads.

In another embodiment, the plurality of protrusions can form an irregular pattern on the outer surface of a sleeve 1504.

It is preferred that the anchor mechanism 1500 is placed about the underlying structure 1502 so that a portion of the underlying structure 1502 extends from each longitudinal end of the anchor mechanism 1500, as is the case in FIGS. 15A-15D. This reduces the chances that the anchor mechanism 1500 will become separated from the underlying structure 1502. In other words, it is preferred that the anchor mechanism 1500 not be attached to just one longitudinal end of the underlying structure 1502, which would increase the possibility that the anchor mechanism 1500 may separate from the underlying structure 1502, e.g., if the underlying structure slips out. Also, where the anchor mechanism 1500 does not extend from one of the longitudinal ends of the underlying structure 1502, the anchor mechanism 1500 does not lengthen the underlying structure 1502. This is beneficial in that the anchor mechanism will not affect the depths at which the underlying structure can be implanted, nor will it affect the distances that can be achieved between a pair of underlying structures (e.g., a pair of radioactive seeds). Additionally, this will allow for more precise placement of the structure 1500 during implantation.

For a portion of the underlying structure 1502 to extend from each longitudinal end of the anchor mechanism 1500, the longitudinal length of the anchor mechanism 1500 (i.e., the length of the sleeve 1504) should be less than the length of the underlying structure 1502. Additionally, for a portion of the underlying structure 1502 to extend from each longitudinal end of the anchor mechanism 1500, the bore 1508 should extend the entire length of the anchor mechanism.

In accordance with specific embodiments of the present invention, where the underlying structure is a radioactive seed, a plurality of radioactive seeds, with an anchor mechanism 1500 of the present invention fit around each of the seeds (or at least some of the seeds), can be loaded into a cartridge. Examples of such a cartridge (e.g., 934) were discussed above with reference to FIG. 9. This would enable the seeds, with the anchor mechanisms 1500 fit around them, to be implanted into patient tissue using an applicator, such as applicator 900 described with reference to FIG. 9.

Embodiments of the present invention are also directed to therapeutic members for use in brachytherapy and other radiation treatment. In accordance with an embodiment such a therapeutic member includes an underlying structure (e.g., a radioactive source, a thermal ablation implant, a spacer, a strand or a radiopaque marker), with a sleeve to fit around the structure. The sleeve has a bore that extends an entire longitudinal length of the sleeve, and through which the structure fits, such that a portion of the structure extends out from each longitudinal end of the sleeve. One or more protrusion extends from the sleeve for engaging the patient tissue after implantation of the therapeutic member, to thereby reduce a tendency for the therapeutic member to migrate and rotate after implantation.

As described above, therapeutic members of the present invention can be manufactured in various manners, including by molding an encapsulating bio-absorbable material around a radioactive source (an encapsulating structure is also referred to herein as an outer structure). Referring to FIG. 16A, a mold 1650 for forming a therapeutic member according to an embodiment of the present invention can comprise two-pieces 1652, 1654 that when closed define a cavity shaped as an inverse of a desired pattern of the encapsulating bio-absorbable material. Referring to FIG. 16B, a therapeutic member formed in the mold 1650 includes an encapsulating, bio-absorbable material 1604 resembling the pattern of FIGS. 6A and 6B. The pattern includes ribs 1608 encircling an underlying radioactive source 1602. The leading edge and trailing edge of the pattern also includes ribs 1609 that extend over the ends of the therapeutic member. Such ribs 1609 as shown not only in FIGS. 16A and 16B, but also FIGS. 6A and 6B, can be referred to as endcap ribs. The pattern of FIG. 16B is merely exemplary, and molds for forming therapeutic members can result in myriad different patterns.

A residual product of the molding process is flash or flashing, which is excess material attached to the encapsulating bio-absorbable material 1604. Flash can result from leakage of encapsulating material between surfaces of a mold, for example at a parting line between the mated surfaces of the two-pieces 1652, 1654 of the mold 1650. Flash can be removed from the therapeutic member 1600, or alternatively at least a portion can be retained to form a rail 1605. Before or after the therapeutic member 1600 is removed from the mold 1650, the flash can optionally be trimmed and/or shaped to extend from the encapsulating bio-absorbable material 1604 a desired distance.

Referring to FIG. 16C, a rail 1605 increases a width of the therapeutic member 1600 beyond a width of the inner diameter of a needle 1620 that is to be used to implant the therapeutic member. The rail 1605 at least partially collapses when the therapeutic member 1600 is positioned within the needle 1620; however, the elastic properties of the encapsulating material will cause the rail 1605 to exert a force against the inner diameter of the needle 1620. The force of the rail against the inner diameter of the needle resists movement of the therapeutic member within the needle. Further, the force of the rail against the inner diameter of the needle provides a positive feedback to a physician, so that the physician can observe a change in resistance to estimate when the therapeutic member is expelled out of a distal end of the needle and deposited at a target location and no longer held within the needle. Still further, the rail can tie external features of encapsulating bio-absorbable material patterns together for strength and structural integrity so that the external features are not torn or otherwise damaged during therapeutic member loading and implantation, including while the therapeutic member is being pushed through the hollow needle. For example, the rail 1605 bridges the ribs 1608 of the therapeutic member 1600 of FIG. 16B.

Figure 17A:
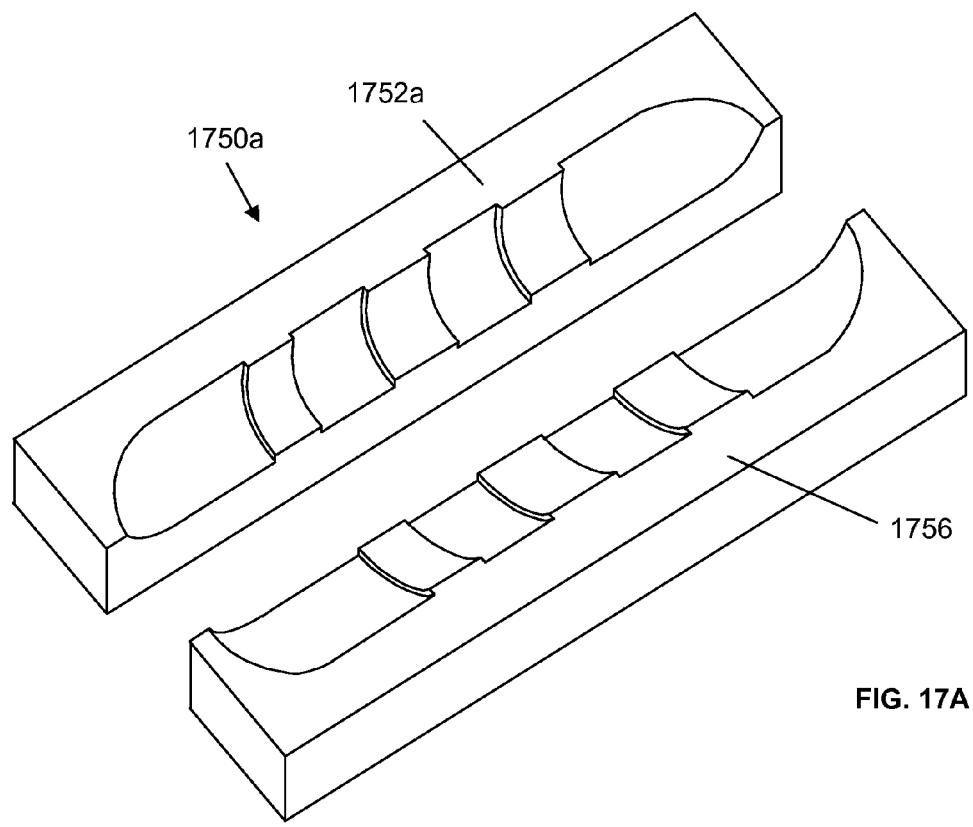
FIG. 17A is a partial perspective view of a mold divided into quarters for forming a therapeutic member according to an alternative embodiment of the present invention.

FIG. 17A is a partial perspective view of a mold for forming a therapeutic member 1700 according to an alternative embodiment of the present invention. The mold 1750a is quartered (only two pieces 1752a, 1756 of the mold 1750a are shown) so that parting lines extend along perpendicular axes. Referring to FIGS. 17C and 17D, rails 1705, 1707 extending from the encapsulating bio-absorbable material 1704 are formed from flash generated at the parting lines and, as above, can provide resistance movement of the therapeutic member 1700 within the needle and provide a positive feedback to the physician, so that the physician can observe a change in resistance to estimate when the therapeutic member is expelled out of a distal end of a needle and deposited at a target location and no longer within the needle. As shown in FIG. 17E, rails 1705, 1707 spanning the therapeutic member 1700 can further assist in approximately centering the radioactive source 1702 within the needle 1720. The rails span the therapeutic member 1700 along a longitudinal direction, arranged at each 90° interval about the longitudinal axis 1703 of the circular cross-section of the encapsulating bio-absorbable material 1704. The rails 1705, 1707 can reduce contact of other features of the therapeutic member (e.g. the ribs 1708) with an inner diameter of a needle. Thus, for example, if the ribs 1708 and/or spaces between the ribs 1708 are coated with a drug, a hormone, and/or an adhesive, the rails 1705, 1707 can reduce frictional contact that can cause the coating to rub off or stick to the inside of the needle. Further, as with the previous embodiment, the rails 1705, 1707 hold the ribs 1708 together and give strength and structural integrity to the ribs in combination with the rails.

Figure 17B:
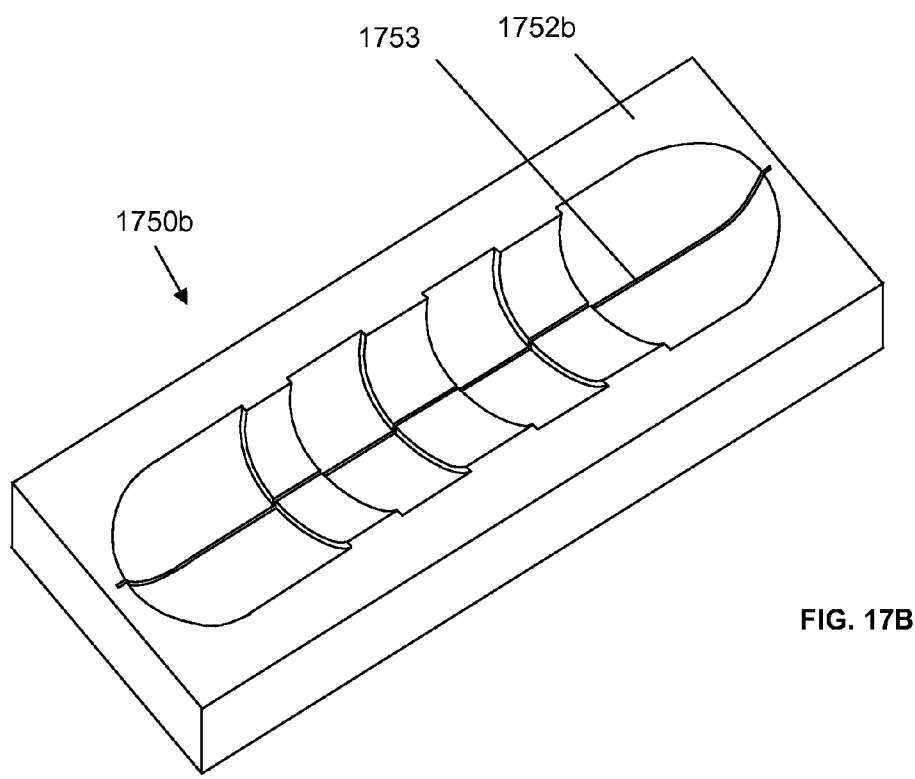
FIG. 17B is a partial perspective view of a mold including a rail cavity for forming the therapeutic member according to the alternative embodiment of the present invention.

Methods for fabricating a therapeutic member including a rail according to the present invention have been described thus far as including retaining and trimming and/or shaping residual product (i.e., flash) from the molding process. However, embodiments of methods for fabricating a therapeutic member including a rail can further comprise using a mold, cast or embossing structure including a pattern that incorporates a rail forming shape. FIG. 17B is a partial perspective view of a mold 1750b including a rail depression 1753 for forming the therapeutic member 1700 of FIGS. 17C-E. A first rail 1707 extending from the therapeutic member in a longitudinal direction is formed by the rail depression 1753 and a second rail 1705 extending from the therapeutic member in a longitudinal direction and aligned in a plane perpendicular to a plane of the first rail is formed by a parting line separating halves 1752*b* of the mold 1750*b*. As will be appreciated, rails can be formed extending from encapsulating material of a therapeutic member having any geometry and protruding in any direction by one or more rail depressions defined in a mold or one or more parting lines separating pieces of the mold, or alternatively a combination of both rail depressions and parting lines.

Figure 18A:
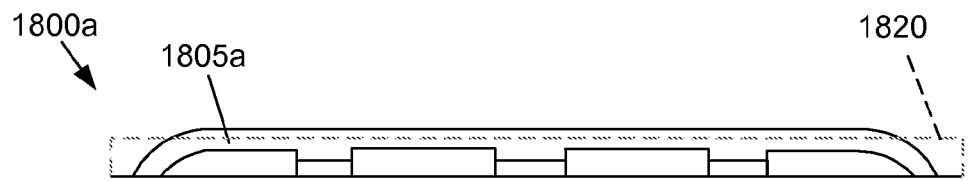
FIG. 18A is a partial side view of a therapeutic member resembling the therapeutic member of FIGS. 16A-16C illustrating the rail.
Figure 18B:
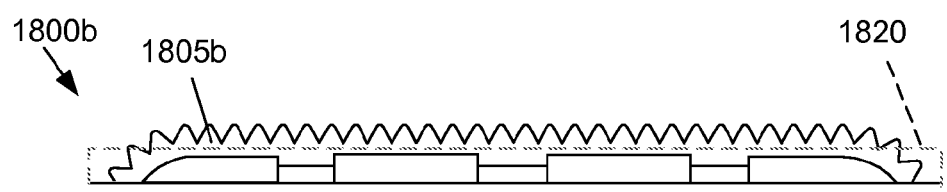
FIG. 18B is a partial side view of a therapeutic member according to an alternative embodiment of the present invention including a rail having a serrated shape.
Figure 18C:
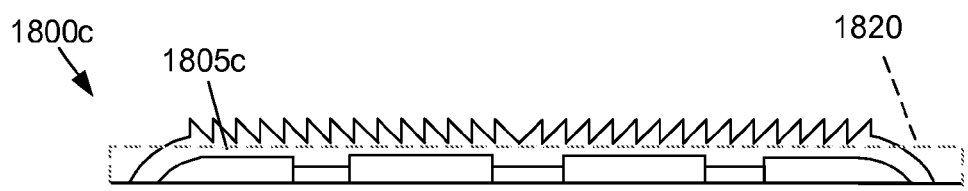
FIG. 18C is a partial side view of a therapeutic member according to an alternative embodiment of the present invention including a rail having a saw-tooth shape.
Figure 18D:
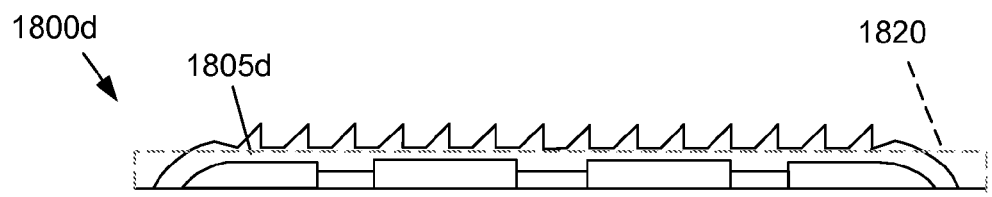
FIG. 18D is a partial side view of a therapeutic member according to a further embodiment of the present invention including a rail having a gapped saw-tooth shape.

Referring to FIG. 18A, the rail 1805*a* can be trimmed so that an outer diameter of the therapeutic member 1800*a* exceeds an inner diameter of a needle 1820 by an amount (e.g. 10%) determined to provide a desired amount of resistance to movement within the needle. Rail thickness can vary along the rail length, which thickness changes the elastic response of the rail. For example, rail thickness can vary with the outer diameter of the therapeutic member. Optionally, the rail can be shaped. For example, in other embodiments the rail 1805*b* can be serrated (FIG. 18B), the rail can be saw-toothed in opposing directions (FIG. 18C), and the rail can be saw-toothed with gapped protrusions (FIG. 18D). Serrated rails and saw-toothed rails can provide an additional benefit of anchoring the therapeutic member within an implantation site to resist migration of the therapeutic member. The anchoring can assist other features (such as ribs) that anchor the therapeutic member. As will be appreciated by one of ordinary skill in the art upon reflecting on the teachings provided herein, rails for use with therapeutic members to resist movement of therapeutic members within a delivery vehicle, such as a needle, can have myriad different shapes, patterns, and/or thicknesses. Different rails can have differing performance characteristics within a needle as well as within an implantation site. Further, rails need not be arranged at 180° intervals about a longitudinal axis of the circular cross-section of the therapeutic member (as shown in FIGS. 16A and 16B) or arranged at 90° intervals about a longitudinal axis of the circular cross-section of the therapeutic member (as shown in FIGS. 17A and 17B), but can be arranged at other intervals (e.g. 60°, 120°, etc.) or alternatively can be arranged at varying intervals.

Figure 19A:
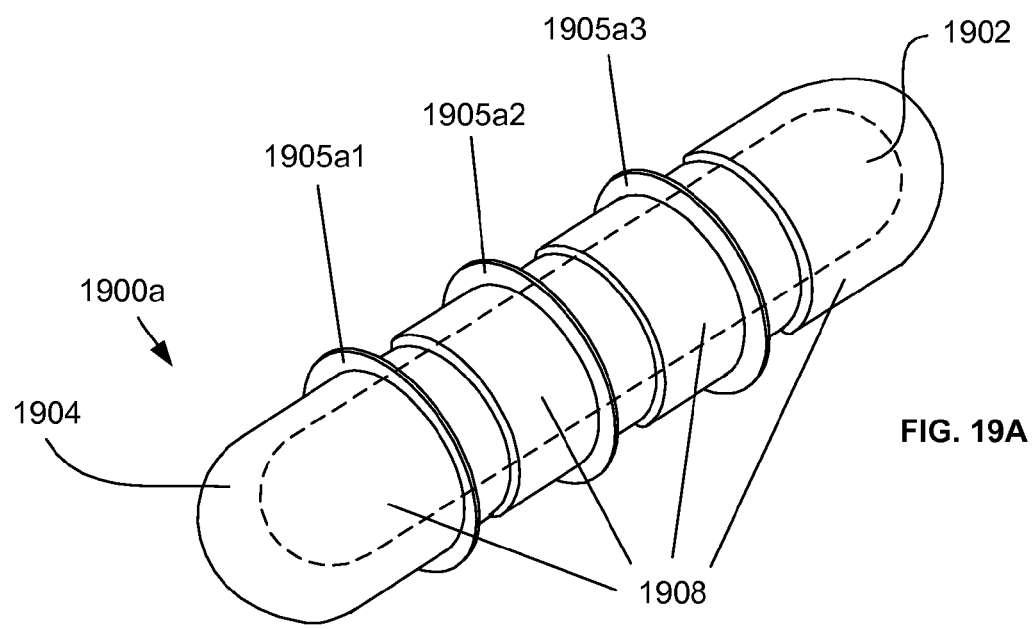
FIG. 19A is a perspective view of a therapeutic member according to an alternative embodiment of the present invention including a plurality of riblets encircling the therapeutic member.
Figure 19B:
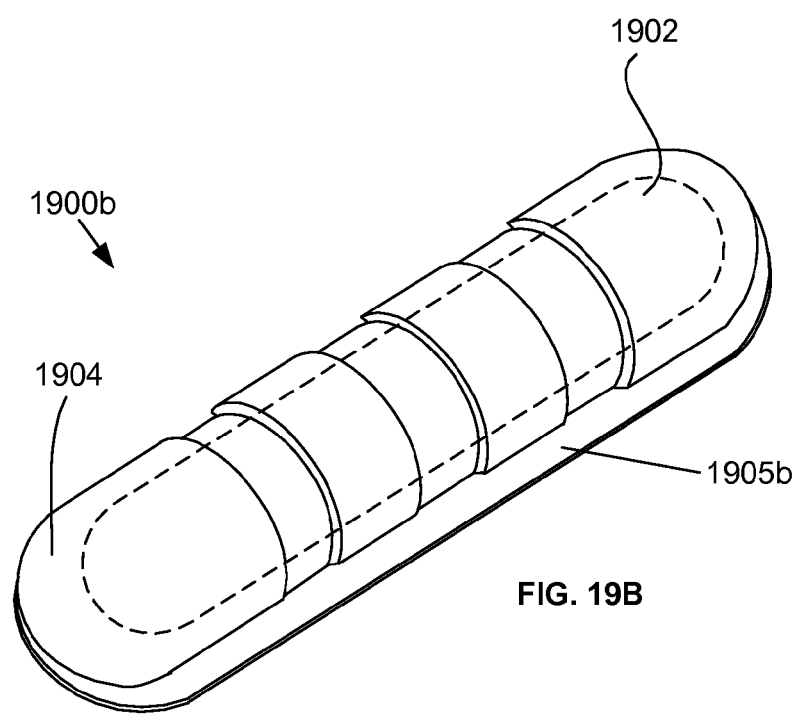
FIG. 19B is a perspective view of a therapeutic member according to a further embodiment of the present invention including a rail extending asymmetrically from the therapeutic member.

Still further, the rail need not be limited to structures that extend along a longitudinal axis of the therapeutic member. Referring to FIG. 19A, in an alternative embodiment a plurality of riblets 1905*a*1, 1905*a*2, 1905*a*3 encircle a therapeutic member 1900*a*, the plurality of riblets extending from a encapsulating bio-absorbable material 1904 encapsulating a radioactive source 1902 or other underlying structure (e.g. marker, coil, spacer, etc.) at approximately a trailing edge of ribs 1908 of the encapsulating material. Referring to FIG. 19B, in a further embodiment a rail 1905*b* can extend asymmetrically from the therapeutic member 1900*b*. In such an embodiment, the radioactive source will likely not be centered; however, the rail 1905*b* can still provide resistance to movement within a needle and indication of delivery to an implant location. In still other embodiments, the rail can wind over the outer surface of the encapsulating bio-absorbable material in a helical fashion along the longitudinal axis (not shown). In further embodiments, the rail can have discontinuities along the length of the rail.

Figure 20A:
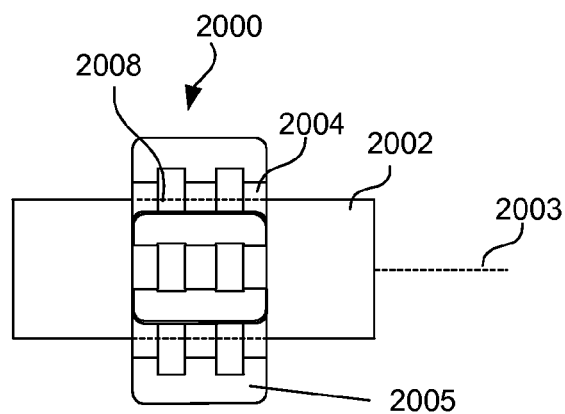
FIG. 20A is a side view of a therapeutic member according to a further embodiment of the present invention.
Figure 20B:
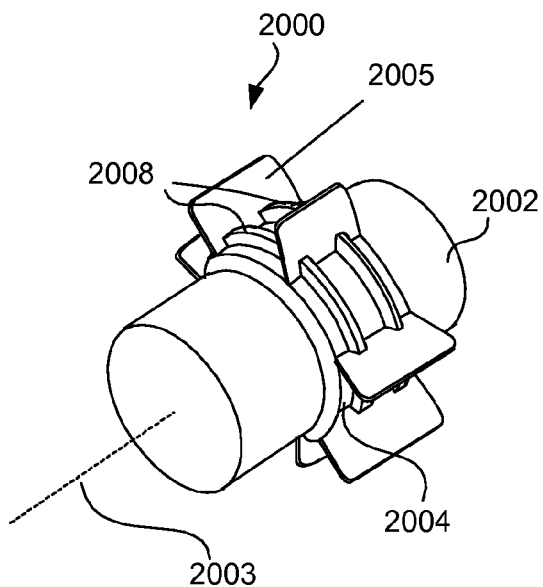
FIG. 20B is a perspective view of the therapeutic member shown in FIG. 20A.

Rails can be incorporated into myriad different patterns, such as those shown in FIGS. 1A-15D. Still further, rails need not be limited in number and spacing to the examples provided in FIGS. 16A-17E. For example, referring to FIGS. 20A and 20B, a sleeve 2004 that only partially encapsulates a radioactive source 2002 or other underlying structure is shown having ribs 2008 that extend from the sleeve 2004. Rails 2005 extend across the sleeve 2004 arranged at 60° intervals about the longitudinal axis 2003 of the circular cross-section of the sleeve 2004. The sleeve 2004 is force fit, glued, heat shrunk or molded at the source 2002 to form the therapeutic member 2000. As above, the rails provide one or more of the benefits of tying external features of sleeve patterns together for strength and structural integrity, approximately centering the radioactive source within a needle, resisting movement of the therapeutic member within the needle, and providing positive feedback as to the deposit of the therapeutic member at an implant site.

While therapeutic members comprising rails and riblets have been described with specific reference to molding, in still further embodiments, therapeutic members manufactured using other techniques can include such features. For example, rails and riblets can be formed by way of mechanical deformation, such as by crimping and cutting.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A therapeutic member for use in brachytherapy deliverable to an implant site by way of a needle, comprising:
   a radioactive source;
   an outer structure encapsulating at least a portion of said radioactive source;
   said outer structure including a plurality of protrusions that reduce a tendency of the therapeutic member to migrate and rotate within a body of a patient after implantation;
   said protrusions including first and second radial ribs encircling said radioactive source and spaced apart from one another along at least a portion of a longitudinal axis of said radioactive source; and
   said outer structure also including one or more longitudinal rails;
   wherein at least a portion of each said longitudinal rail extends between and thereby ties together said first and second radial ribs.

2. The therapeutic member of claim 1, wherein said outer structure comprises a polymeric material molded to encapsulate said at least a portion of said radioactive source.

3. The therapeutic member of claim 1, wherein said outer structure comprises a polymeric material molded to completely encapsulate said radioactive source.

4. The therapeutic member of claim 1, wherein said radioactive source comprises a radioactive seed that includes radioactive material contained within a metallic housing having a substantially smooth outer surface without any protrusions.

5. The therapeutic member of claim 1, wherein each of said one or more longitudinal rails is generally perpendicular to said radial ribs.

6. The therapeutic member of claim 1, wherein:
   said protrusions also include a first end cap rib located at a first longitudinal end of said outer structure and a second end cap rib located at a second longitudinal end of said outer structure;
   said first and second radial ribs encircling said radioactive source are located between said first end cap rib and said second end cap rib; and said first end cap rib, said first and second radial ribs, and said second end cap rib are tied together by each said longitudinal rail.

7. The therapeutic member of claim 1, wherein at least a portion each said longitudinal rail extends further from said radioactive source than said radial ribs in order to substantially center the therapeutic member in a lumen of a needle.

8. The therapeutic member of claim 1, further including at least one material including a drug, hormone or other therapeutic material or an adhesive material coating at least a portion of at least one of said radial ribs or at least a portion of a space between said radial ribs.

9. The therapeutic member of claim 1, wherein at least a portion of a said longitudinal rail includes serrations, teeth and/or irregularities to assist in reducing a tendency of the therapeutic member to migrate and rotate within a body of a patient after implantation.

10. The therapeutic member of claim 1, wherein each of said one or more longitudinal rails is generally parallel to the longitudinal axis of said radioactive source and extends outward from opposite sides of said radioactive source.

11. The therapeutic member of claim 1, further comprising one or more further radioactive sources, each of which is at least partially encapsulated by said outer structure.

12. The therapeutic member of claim 11, wherein said outer structure includes a separate plurality of protrusions associated with each of said radioactive sources.

13. The therapeutic member of claim 12, wherein for each said radioactive source:
  said separate plurality of protrusions associated with the said radioactive source include a first end cap rib, a second end cap rib and first and second radial ribs encircling said radioactive source between said first end cap rib and said second end cap rib; and
  said outer structure includes one or more longitudinal rails that tie together said first end cap rib, said first and second radial ribs encircling said radioactive source, and said second end cap rib.

14. The therapeutic member of claim 12, further comprising a space defined by said outer structure between each adjacent pair of said radioactive sources, wherein at least a portion of said outer structure that defines each said space does not include any protrusions.

15. The therapeutic member of claim 12, wherein for each said radioactive source:
  said separate plurality of protrusions associated with the said radioactive source include first and second radial ribs encircling the said radioactive source and spaced apart from another; and
  said outer structure includes one or more longitudinal rails that tie together said first and second radial ribs.

16. A therapeutic member for use in brachytherapy deliverable to an implant site by way of a needle, comprising:
  a radioactive source;
  an outer structure molded to encapsulate the radioactive source and including
  (a) a first end cap rib located at a first longitudinal end of said outer structure;
  (b) a second end cap rib located at a second longitudinal end of said outer structure;
  (c) one or more radial ribs encircling said radioactive source between said first end cap rib and said second end cap rib; and
  (d) one or more longitudinal rails that tie together said first end cap rib, said one or more radial ribs encircling said radioactive source, and said second end cap rib.

17. The therapeutic member of claim 16, wherein said one or more radial ribs encircling said radioactive source comprise a first radial rib and a second radial rib encircling said radioactive source and spaced apart from one another between said first end cap rib and said second end cap rib.

18. The therapeutic member of claim 16, wherein each of said one or more longitudinal rails is generally perpendicular to each said radial rib encircling said radioactive source.

19. The therapeutic member of claim 16, wherein said radioactive source comprises a radioactive seed that includes radioactive material contained within a metallic housing having a substantially smooth outer surface without any protrusions.

20. A therapeutic member for use in brachytherapy deliverable to an implant site by way of a needle, comprising:
  a radioactive source; and
  a polymeric material molded to encapsulate said radioactive source;
  wherein an outer surface of said polymeric material defines at least two radial ribs spaced apart from on another and encircling said radioactive source and one or more longitudinal rails that tie together said at least two radial ribs; and
  wherein a thickness of the encapsulating polymeric material varies such that the thickness is greater where there is at least one of a said radial rib and a said longitudinal rail than where there is not at least one of a said radial rib and a said longitudinal rail.

21. The therapeutic member of claim 20, wherein said radioactive source comprises a radioactive seed that includes radioactive material contained within a metallic housing having a substantially smooth outer surface without any protrusions.

* * * * *